United States Patent
Baryshyan et al.

(10) Patent No.: US 11,584,784 B2
(45) Date of Patent: Feb. 21, 2023

(54) SYSTEMS AND METHODS FOR MANUFACTURING A SILK FIBROIN SOLUTION AND POWDERS CONTAINING SILK FIBROIN

(71) Applicant: Cambridge Crops, Inc., Boston, MA (US)

(72) Inventors: Amanda Baryshyan, Ipswich, MA (US); Nick Zhang, Newton, MA (US); Jesse Groner, Cambridge, MA (US); Adam Behrens, Boston, MA (US); Nicole Marco, Somerville, MA (US); Samantha Roman, Cambridge, MA (US); Rebeca Lopez-Garcia, Mexico City (MX); Lindsay Perrea, Allston, MA (US); Colin Preston, Salem, MA (US); Laith Abu-Taleb, Gaithersburg, MD (US); Linda Michelle Rauch, Amherst, MA (US); Herve Irenee Garant, III, West Bath, ME (US); John Patrick Ellersick, Cambridge, MA (US)

(73) Assignee: Cambridge Crops, Inc., Boston, MA (US)

( * ) Notice: Subject to any disclaimer, the term of this patent is extended or adjusted under 35 U.S.C. 154(b) by 0 days.

(21) Appl. No.: 17/650,570

(22) Filed: Feb. 10, 2022

(65) Prior Publication Data

US 2022/0372087 A1 Nov. 24, 2022

Related U.S. Application Data

(60) Provisional application No. 63/231,399, filed on Aug. 10, 2021, provisional application No. 63/212,283, (Continued)

(51) Int. Cl.
*B01D 11/02* (2006.01)
*B01D 61/14* (2006.01)
(Continued)

(52) U.S. Cl.
CPC ...... *C07K 14/43586* (2013.01); *A23L 3/3526* (2013.01); *B01D 1/16* (2013.01);
(Continued)

(58) Field of Classification Search
CPC ............ B01D 11/0257; B01D 11/0261; B01D 37/048; B01D 61/14; B01D 2315/10;
(Continued)

(56) References Cited

U.S. PATENT DOCUMENTS

| 4,233,212 A | 11/1980 | Otoi et al. |
| 4,608,203 A | 8/1986 | Akasaka et al. |

(Continued)

FOREIGN PATENT DOCUMENTS

| CN | 103739691 A | 4/2014 |
| EP | 0352330 A1 | 1/1990 |

(Continued)

OTHER PUBLICATIONS

World Intellectual Property Organization, International Search Report for PCT/US2022/070619, dated May 24, 2022.
(Continued)

*Primary Examiner* — Jeffrey E. Russel
(74) *Attorney, Agent, or Firm* — Womble Bond Dickinson (US) LLP; John V. Forcier

(57) ABSTRACT

The disclosure relates to systems and methods for improving the manufacturing of silk solutions and powders containing silk fibroin obtained from silkworm cocoons. The methods include use of a reactor vessel to degum, rinse, and dissolve the silk fibroin protein from silk inputs to obtain a food grade silk powder. The reactor vessel may include a combination
(Continued)

of inputs and outputs for introducing and removing different components used or generated during the process. The systems may include any combination of heat exchangers, holding tanks, filtration modules, and post-treatment equipment as necessary to obtain the silk powder. The solutions and powders can be used to improve the post-harvest preservation of perishables and to improve the performance of packaging, including biodegradable packaging.

28 Claims, 15 Drawing Sheets

Related U.S. Application Data filed on Jun. 18, 2021, provisional application No. 63/191,441, filed on May 21, 2021.

(51) Int. Cl.
| | |
|---|---|
| *C07K 14/435* | (2006.01) |
| *C07K 1/14* | (2006.01) |
| *B01D 63/10* | (2006.01) |
| *A23L 3/3526* | (2006.01) |
| *B01D 61/22* | (2006.01) |
| *B01D 37/04* | (2006.01) |
| *B01D 1/16* | (2006.01) |

(52) U.S. Cl.
CPC ...... *B01D 11/0257* (2013.01); *B01D 11/0261* (2013.01); *B01D 37/048* (2013.01); *B01D 61/14* (2013.01); *B01D 61/147* (2013.01); *B01D 61/22* (2013.01); *B01D 63/10* (2013.01); *C07K 1/145* (2013.01); *A23V 2002/00* (2013.01); *B01D 2315/10* (2013.01); *B01D 2315/16* (2013.01)

(58) Field of Classification Search
CPC .... B01D 1663/10; B01D 63/10; C07K 1/145; C07K 1/36; C07K 14/43586; C07K 1/045; C07K 1/1045; B01J 8/085; B01J 8/10; B01J 2208/00858; B01J 2208/00884
See application file for complete search history.

(56) References Cited

U.S. PATENT DOCUMENTS

| | | | |
|---|---|---|---|
| 4,940,662 | A | 7/1990 | Yamazaki et al. |
| 5,853,764 | A | 12/1998 | Tsubouchi |
| 6,592,794 | B1 | 7/2003 | Bachrach |
| 7,553,634 | B1 | 6/2009 | Lakhotia et al. |
| 8,309,689 | B2 | 11/2012 | Yang et al. |
| 8,354,501 | B2 | 1/2013 | Kaplan et al. |
| 9,175,052 | B2 | 11/2015 | Gerardi et al. |
| 9,731,052 | B2 | 8/2017 | Kaplan et al. |
| 10,271,561 | B2 | 4/2019 | Omenetto et al. |
| 10,533,037 | B2 | 1/2020 | Wang et al. |
| 2005/0197496 | A1 | 9/2005 | Perreault |
| 2006/0273279 | A1 | 12/2006 | Kaplan et al. |
| 2008/0166469 | A1 | 7/2008 | Schweizer et al. |
| 2009/0110651 | A1* | 4/2009 | Moussou ............ A61K 8/9789 424/62 |
| 2011/0014287 | A1 | 1/2011 | Altman et al. |
| 2014/0378661 | A1 | 12/2014 | Lo et al. |
| 2015/0183841 | A1 | 7/2015 | Lo et al. |
| 2015/0337008 | A1 | 11/2015 | Montagner et al. |
| 2016/0046679 | A1 | 2/2016 | Kluge et al. |
| 2016/0185817 | A1 | 6/2016 | Zhu et al. |
| 2016/0206780 | A1 | 7/2016 | Wang |
| 2016/0215030 | A1 | 7/2016 | Bressner et al. |
| 2018/0310604 | A1 | 11/2018 | Rubin |
| 2018/0352833 | A1 | 12/2018 | Zhang et al. |
| 2019/0069590 | A1 | 3/2019 | Neal et al. |
| 2019/0070088 | A1 | 3/2019 | Altman et al. |
| 2019/0309467 | A1 | 10/2019 | Altman et al. |
| 2021/0094982 | A1* | 4/2021 | Ludemann-Hombourger ............ G01N 21/65 |
| 2022/0177530 | A1* | 6/2022 | Altman .................. C08J 7/0427 |

FOREIGN PATENT DOCUMENTS

| | | |
|---|---|---|
| EP | 1869238 B1 | 7/2009 |
| EP | 2154990 B1 | 6/2013 |
| EP | 2475677 B1 | 8/2018 |
| EP | 2934187 B1 | 7/2019 |
| EP | 3645063 A1 | 5/2020 |
| WO | WO-2007016524 A2 | 2/2007 |
| WO | WO-2012145739 A1 | 10/2012 |
| WO | WO-2014145002 A2 | 9/2014 |
| WO | WO-2015134865 A1 | 9/2015 |
| WO | WO-2019094700 A1 | 5/2019 |
| WO | WO-2020028918 A1 | 2/2020 |

OTHER PUBLICATIONS

Ajisawa, "Dissolution of silk fibroin with calcium chloride/ethanol aqueous solution," J. Seric. Sci. Jpn., 67(2):91-94, (1998).

Ali et al., "Gum arable as a novel edible coating for enhancing shelf-life and improving postharvest quality of tomato (*Solanum lycopersicum* L.) fruit," Postharvest Biology and Technology, 58:42-47, (2010).

Basal et al., "Antibacterial Properties of Silk Fibroin/Chitosan Blend Films Loaded with Plant Extract," Fibers and Polymers, 11(1):21-27, (2010).

Boulet-Audet et al., "Dry-Spun Silk Produces Native-Like Fibroin Solutions," Biomacromolecules, 17(10):3198-3204, (2016).

Cheng et al., "Differences in regenerated silk fibroin prepared with different solvent systems: From structures to conformational changes," J. Appl. Polym. Sci., 41959:1-8, (2015).

Day, BPF. "Fruit and Vegetables." Principles and Applications of Modified Atmosphere Packaging of Foods, Springer-Verlag, 1993, pp. 114-133.

Freddi et al., "Swelling and dissolution of silk fibroin (*Bombyx mori*) in N-methyl morpholine N-oxide," Int J Biol Macromol, 24(2-3):251-263, (1999).

Fuchs et al., "Effect of Edible Coatings on Postharvest Quality of Fresh Green Asparagus," Journal of Food Processing and Preservation, 32:951-971, (2008).

Furuhata et al., "Dissolution of silk fibroin in lithium halide/organic amide solvent systems," J. Seric. Sci. Jpn., 63(4):315-322, (1994).

Gobin et al., "Structural and mechanical characteristics of silk fibroin and chitosan blend scaffolds fortissue regeneration," J Biomed Mater Res A, 74(3):465-473, (2005).

Gong et al., "Two distinct beta-sheet fibrils from silk protein," Chem Commun (Camb), (48):7506-7508, (2009).

Haggag et al., "Degumming of Silk Using Micro wave-Assisted Treatments," Journal of Natural Fibers, 4(3):1-22, (2007).

Hino et al., "Change in secondary structure of silk fibroin during preparation of its microspheres by spray drying and exposure to humid atmosphere," J Colloid Interface Sci, 266(1):68-73, (2003).

Hu et al., "Determining Beta-Sheet Crystallinity in Fibrous Proteins by Thermal Analysis and Infrared Spectroscopy," Macromolecules, 39:6161-6170, (2006).

International Search Report and Written Opinion for PCT/US19/65268, dated Mar. 23, 2020.

Jaramillo-Quiceno et al., "Water-annealing treatment for edible silk fibroin coatings from fibrous waste," J. Appl. Polym. Sci, 48505:1-8, (2019).

Kamalha et al., "Analysis of the secondary crystalline structure of regenerated *Bombyx mori* fibroin," RRBS, 7(2):76-83, (2013).

Khalifa et al., "Application of sericin to modify textile supports," The Journal of Textile Institute, 103(4):370-377, (2012).

Khan et al., "Physical properties and dyeability of silk fibers degummed with citric acid," Bioresour Technol, 101(21):8439-8445, (2010).

(56) References Cited

OTHER PUBLICATIONS

Kim et al., "Formulation of Biologically-Inspired Silk-Based Drug Carriers for Pulmonary Delivery Targeted for Lung Cancer," Sci Rep, 5:11878, (2015).
Kluge et al., "Optimizing molecular weight of lyophilized silk as a shelf-stable source material," ACS Biomater. Sci. Eng., (2016).
Kluge et al., "Silk-based blood stabilization for diagnostics," Proc Natl Acad Sci U S A, 113(21):5892-5897, (2016).
Koh et al., "Structures, mechanical properties and applications of silk fibroin materials," Progress in Polymer Science, 46:86-110, (2015).
Kundu et al., "Isolation and processing of silk proteins for biomedical applications," Int J Biol Macromol, 70:70-77, (2014).
Kweon et al., "Dissolution and Characterization of Regenerated *Antheraea pernyi* Silk Fibroin," Journal of Applied Polymer Science, 82:750-758, (2001).
Li et al., "Silk-based stabilization of biomacromolecules," J Control Release, 219:416-430, (2015).
Li et al., "Regenerated silk materials for functionalized silk orthopedic devices by mimicking natural processing," Biomaterials, 110:24-33, (2016).
Li et al., "Enhanced Stabilization in Dried Silk Fibroin Matrices," Biomacromolecules, 18:2900-2905, (2017).
Li et al., "Fabrication and characterization of microencapsulated n-octadecane with silk fibroin-silver nanoparticles shell for thermal regulation," Journal of Materials Research, 34(12):2047-2056, (2019).
Lin et al., "Cold plasma treated thyme essential oil/silk fibroin nanofibers against *Salmonella typhimurium* in poultry meat," Food Packaging and Shelf Life, 21:100337, (2019).
Liu et al., "Exploring the Structural Transformation Mechanism of Chinese and Thailand Silk Fibroin Fibers and Formic-Acid Fabricated Silk Films," Int J Mol Sci, 19(11), 2018).
Lu et al., "Stabilization of Enzymes in Silk Films," Biomacromolecules, 10:1032-1042, (2009).
Lu et al., "Stabilization and Release of Enzymes from Silk Films," Macromol. Biosci., 10:359-368, (2010).
Malay et al., "Relationships between physical properties and sequence in silkworm silks," Sci Rep, 6:27573, (2016).
Marelli et al., "Silk Fibroin as Edible Coating for Perishable Food Preservation," Sci Rep, 6:25263, (2016).
Marelli et al., Supporting Information, "Silk Fibroin as Edible Coating for Perishable Food Preservation," Sci Rep, 6:25263, (2016).
Meng et al., "Controllable in situ synthesis of silver nanoparticles on multilayered film-coated silk fibers for antibacterial application," J Colloid Interface Sci, 461:369-375, (2016).
Meshram et al., "Extraction of lithium from primary and secondary sources by pre-treatment, leaching and separation: A comprehensive review," Hydrometallurgy, 150:192-208, (2014).
Pawcenis et al., "Size exclusion chromatography for analyses of fibroin in silk: optimization of sampling and separation conditions," Appl. Phys. A, 114:301-308, (2014).
Pritchard et al., "Encapsulation of Oil in Silk Fibroin Biomaterials," J. Appl. Polym. Sci., 39990:1-11, (2014).
Rnjak-Kovacina et al., "The effect of sterilization on silk fibroin biomaterial properties," Macromol Biosci, 15(6):861-874, (2015).
Rockwood et al., "Materials fabrication from *Bombyx mori* silk fibroin," Nat Protoc, 6(10):1612-1631, (2011).

Sah et al., "The extraction of fibroin protein from *Bombyx mori* silk cocoon: Optimization of process parameters," International Journal of Bioinformatics Research, 2(2):33-41, (2010).
Saha et al., "Extraction, Structural and Functional Properties of Silk Sericin Biopolymer from *Bombyx mori* Silk Cocoon Waste," J Textile Sci Eng, 9(1):1000390, (2019).
Sashina et al., "Dissolution of Silk Fibroin in N-methylmorpholine-N-oxide and Its Mixtures with Organic Solvents," Russian Journal of Applied Chemistry, 76(1):128-131, (2003).
Sashina et al., "Structure and Solubility of Natural Silk Fibroin," Russian Journal of Applied Chemistry, 79(6):869-876, (2006).
Shen et al., "Dissolution behavior of silk fibroin in a low concentration $CaCl_2$-methanol solvent: From morphology to nanostructure," Int J Biol Macromol, 113:458-463, (2018).
Silva et al., "Glycerin and Ethanol as Additives on Silk Fibroin Films: Insoluble and Malleable Films," J. Appl. Polym. Sci., (2013).
Sparkes et al., "Analysis of the pressure requirements for silk spinning reveals a pultrusion dominated process," Nat Commun, 8(1):594, (2017).
Srihanam et al., "Silk fibroin microspheres prepared by the water-in-oil emulsion solvent diffusion method for protein delivery," Korean J. Chem. Eng., 28(1):293-297, (2011).
Tabatabai et al., "Acid induced assembly of a reconstituted silk protein system," (2018).
Toms et al., "Determination of the Configuration of Silk Fibroin Dissolved in Aqueous Solutions of Lithium Bromide," Nature, 169:877-878, (1952).
Vaithanomsat et al., "Production of Water-Soluble Silk Powder from Bombyx mori Lin. (Nang-Noi Srisakate 1)," Kasetsart J. (Nat. Sci.), 40:152-158, (2006).
Vepari et al., "Silk as a Biomaterial," Prog Polym Sci, 32(8-9):991-1007, (2007).
Wang et al., "Colloidal Stability of Silk Fibroin Nanoparticles Coated with Cationic Polymer For Effective Drug Delivery," ACS Appl Mater Interfaces, 7(38):21254-21262, (2015).
Wang et al., "Effect of silk degumming on the structure and properties of silk fibroin," The Journal of the Textile Institute, (2018).
Wray et al., "Effect of processing on silk-based biomaterials: reproducibility and biocompatibility," J Biomed Mater Res B Appl Biomater, 99(1):89-101, (2011).
Wu et al., "Control of silk microsphere formation using polyethylene glycol (PEG)," Acta Biomaterialia, (2016).
Wu et al., "Nanofiltration recovery of sericin from silk processing waste and synthesis of a lauroyl sericinbased surfactant and its characteristics," RSC Adv., 4:4140-4145, (2014).
Yamada et al., "Preparation of undegraded native molecular fibroin solution from silkworm cocoons," Materials Science and Engineering C, 14:41-46, (2001).
Yazawa et al., "Influence of Water Content on the ?-Sheet Formation, Thermal Stability, Water Removal, and Mechanical Properties of Silk Materials," Biomacromolecules, 17(3):1057-1066, (2016).
Zheng et al., "Lithium-free processing of silk fibroin," Journal of Biomaterials Applications, 31(3):450-463, (2016).
Zong et al., "Effect of pH and Copper(II) on the Conformation Transitions of Silk Fibroin Based on EPR, NPR, and Raman Spectroscopy," Biochemistry, 43:11932-11941, (2004).

\* cited by examiner

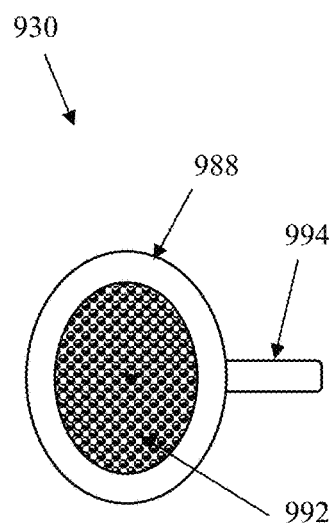
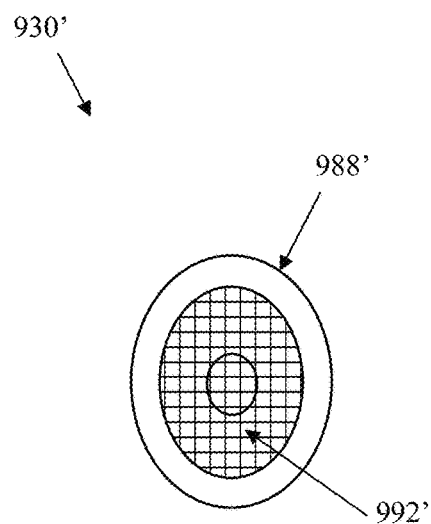
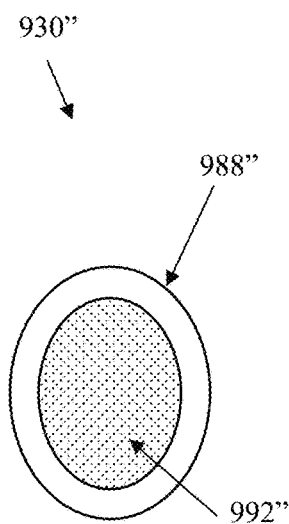
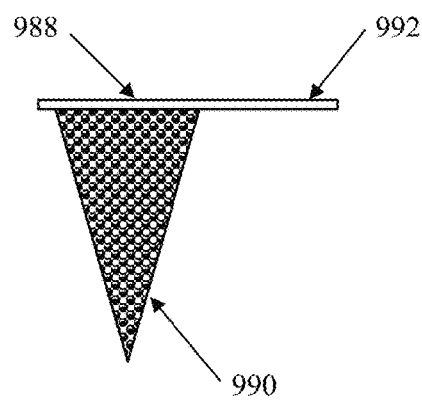
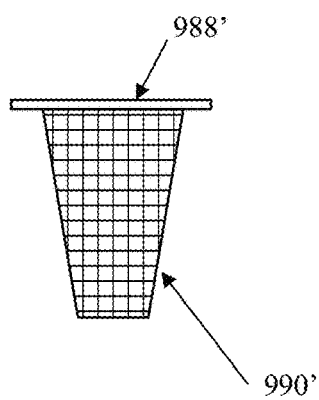
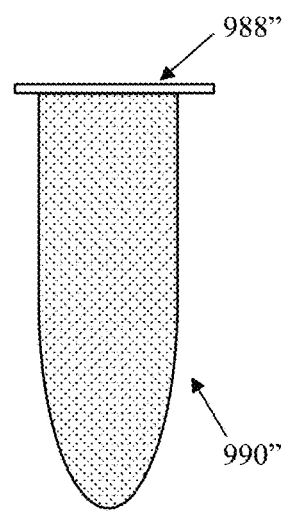
FIG. 9A          FIG. 9B          FIG. 9C

SYSTEMS AND METHODS FOR MANUFACTURING A SILK FIBROIN SOLUTION AND POWDERS CONTAINING SILK FIBROIN

CROSS-REFERENCE TO RELATED APPLICATIONS

This application claims priority to and the benefit of U.S. Provisional Patent Application No. 63/191,441, filed May 21, 2021; U.S. Provisional Application No. 63/212,283, filed Jun. 18, 2021; and U.S. Provisional Application No. 63/231, 399, filed Aug. 10, 2021, which applications are hereby incorporated by reference in their entireties.

FIELD OF THE INVENTION

The disclosure relates to systems and methods for improving the manufacturing of silk solutions containing silk fibroin from silk inputs and the manufacturing of silk fibroin powders derived therefrom.

BACKGROUND

One third of the food produced in the world is wasted each year and over 45% of all fruits and vegetables are lost to spoilage. Food waste has massive economic, social, and environmental implications. According to the Natural Resources Defense Council (NRDC), a prominent non-profit international environmental advocacy group, the United States loses 40% of its food supply resulting in an estimated economic loss of $165 billion per year. Embodiments of the present disclosure directly address the broader societal need for reducing food waste and increasing food availability by extending the shelf-life of perishables (e.g., cooked or uncooked meats, proteins, carbohydrates, produce, nuts, grains, seeds, dairy, beverages, processed foods (e.g., chocolates, candies, chips, snacks, energy bars), gums, tablets, capsules, plants, roots, fungi, spores, breads, dried fruits, dried vegetables, dehydrated foods, medical foods, flowers, plants, and the like). Embodiments of the present disclosure represent significant commercial value by increasing revenue through improved distribution, reducing waste, and decreasing costs associated with cold storage and transport.

SUMMARY OF THE INVENTION

The disclosure relates to systems and methods for improving the manufacturing of silk solutions and powder containing silk fibroin obtained from silk inputs, which can be used to improve the post-harvest preservation of perishables and to improve the performance of packaging, including biodegradable packaging.

In one embodiment, the disclosure provides a manufacturing process for silk fibroin, where a silk source or silk input, such as silk cocoons (the silk cocoons can be whole, including the silkworm pupae, or be processed to remove the pupae and/or be cut in a specific manner), silk sheets, silk floss, or silk pellets, cut cocoons, shredded cocoons, silk yarns and threads, silk textiles, silk powder, silk grinds, silk wadding, silk protein, degummed silk, silk mats, silk webbing, silk fibers, or the like, is processed into a solution or a powder that includes silk fibroin. For example, from a *Bombyx mori* silkworm is an example of a silk source that may be used in this process. This disclosure also applies to silk sources from silkworms other than the *Bombyx mori* (e.g., *Bombyx mandarina, Bombyx sinesis, Anaphe molo-neyi, Anaphe panda, Anaphe reticulate, Anaphe ambrizia, Anaphe carteri, Anaphe venata, Anapha infracta, Antheraea assamensis, Antheraea assama, Antheraea mylitta, Antheraea pernyi, Antheraea yamamai, Antheraea polyphemus, Antheraea oculea, Anisota sanatoria, Apis mellifera, Araneus diadematus, Araneus cavaticus, Automeris io, Atticus atlas, Copaxa multifenestrata, Coscinocera hercules, Callosamia promethea, Eupackardia calleta, Eurprosthenops australis, Gonometa postica, Gonometa rufobrunnea, Hyalophora cecropia, Hyalophora euryalus, Hyalophora gloveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Samia cynthia*, and *Samia ricini*, and *Tetragnatha versicolor*), as well as spiders, or other insects. This disclosure also applies to silk sources generated synthetically, by genetic recombination, transgenically, and other engineered silk (e.g., silks from bacteria, yeast, mammalian cells, transgenic animals, or transgenic plants). Silk proteins have a unique amino acid sequence repeatable via synthetic forms. This disclosure relates to such forms. For the avoidance of doubt, silk cocoons as described herein may be substituted for any of the above forms of silk, or similar forms of silk, be that natural or artificial. For example, if the disclosure states silk, silk inputs, silk cocoons, or silkworm cocoons are used, that means that any of the silk sources discussed in this paragraph (e.g., cocoons, floss, sheets, pellets, cut cocoons, shredded cocoons, silk yarns and threads, silk textiles, silk powder, silk grinds, silk wadding, silk protein, degummed silk, silk mats, silk webbing, silk fibers, generated silk sources (e.g., generated synthetically, by genetic recombination, transgenically, and other engineered silk), etc.) or a combination thereof may be used. In one embodiment, the silk cocoons are subjected to a degumming step, a dissolution step, a purification step, a microfiltration step, and a powderization step, which results in a powder of the silk solution containing silk fibroin. In some embodiments, the silk fibroin may be isolated from the silk cocoons through the Ajisawa method or through other methods using water and salts, including chaotropic and/or kosmotropic agents. In some embodiments, silk fibroin may be prepared according to the method described in Marelli, B., Brenckle, M., Kaplan, D. et al. Silk Fibroin as Edible Coating for Perishable Food Preservation. Sci Rep 6, 25263 (2016), https://doi.org/10.1038/srep25263, incorporated herein by reference in its entirety. The microfiltration step discussed herein would work with any acceptable method of isolating silk fibroin from silk cocoons, including instances where the silk fibroin is processed into a silk solution or as a powder. In some embodiments, the silk fibroin may be as described in US Patent Publication No. 2020-0178576 A1, incorporated herein by reference in its entirety.

In some embodiments the silk fibroin present in an aqueous solution or powder may have a weight concentration (w/w) range from about 0.1% (w/w) to about 1% (w/w), 0.1% (w/w) to about 10% (w/w), 0.1% (w/w) to about 30% (w/w), 0.1% (w/w) to about 50% (w/w), from about 1% (w/w) to about 5% (w/w), from about 1% (w/w) to about 10% (w/w), from about 1% (w/w) to about 15% (w/w), from about 5% (w/w) to about 10% (w/w), from 5% (w/w) to about 15% (w/w), from 5% (w/w) to about 20% (w/w), from 10% (w/w) to about 30% (w/w), from 10% (w/w) to about 100% (w/w), from 50% (w/w) to about 75% (w/w), from 10% (w/w) to about 100% (w/w), from about 20% (w/w) to about 95% (w/w), from about 30% (w/w) to about 90% (w/w), 30% (w/w) to about 100% (w/w), from about 40% (w/w) to about 85% (w/w), from about 50% (w/w) to about 80% (w/w), from about 60% (w/w) to about 99% (w/w), from about 70% (w/w) to about 99% (w/w), from about 80% (w/w) to about 99% (w/w), from about 80% (w/w) to about 100% (w/w), from about 90% (w/w) to about 99% (w/w), from about 95% (w/w) to about 99% (w/w), from about 90% (w/w) to about 100% (w/w), or from about 80% (w/w) to about 90% (w/w). In an embodiment, the percent silk fibroin (w/w) present in an aqueous solution or powder is less than 99%. In an embodiment, the percent silk fibroin (w/w) present in an aqueous solution or powder is less than 95%. In an embodiment, the percent silk fibroin (w/w) present in an aqueous solution or powder is less than 60%. In an embodiment, the percent silk fibroin (w/w) present in an aqueous solution or powder is less than 30%. In an embodiment, the percent silk fibroin (w/w) present in an aqueous solution or powder is less than 25%. In an embodiment, the percent silk fibroin (w/w) present in an aqueous solution or powder is less than 20%. In an embodiment, the percent silk fibroin (w/w) present in an aqueous solution or powder is less than 19%. In an embodiment, the percent silk fibroin (w/w) present in an aqueous solution or powder is less than 18%. In an embodiment, the percent silk fibroin (w/w) present in an aqueous solution or powder is less than 17%. In an embodiment, the percent silk fibroin (w/w) present in an aqueous solution or powder is less than 16%. In an embodiment, the percent silk fibroin (w/w) present in an aqueous solution or powder is less than 15%. In an embodiment, the percent silk fibroin (w/w) present in an aqueous solution or powder is less than 14%. In an embodiment, the percent silk fibroin (w/w) present in an aqueous solution or powder is less than 13%. In an embodiment, the percent silk fibroin (w/w) present in an aqueous solution or powder is less than 12%. In an embodiment, the percent silk fibroin (w/w) present in an aqueous solution or powder is less than 11%. In an embodiment, the percent silk fibroin (w/w) present in an aqueous solution or powder is less than 10%. In an embodiment, the percent silk fibroin (w/w) present in an aqueous solution or powder is less than 9%. In an embodiment, the percent silk fibroin (w/w) present in an aqueous solution or powder is less than 8%. In an embodiment, the percent silk fibroin (w/w) present in an aqueous solution or powder is less than 7%. In an embodiment, the percent silk fibroin (w/w) present in an aqueous solution or powder is less than 6%. In an embodiment, the percent silk fibroin (w/w) present in an aqueous solution or powder is less than 5%. In an embodiment, the percent silk fibroin (w/w) present in an aqueous solution or powder is less than 4%. In an embodiment, the percent silk fibroin (w/w) present in an aqueous solution or powder is less than 3%. In an embodiment, the percent silk fibroin (w/w) present in an aqueous solution or powder is less than 2%. In an embodiment, the percent silk fibroin (w/w) present in an aqueous solution or powder is less than 1%. In an embodiment, the percent silk fibroin (w/w) present in an aqueous solution or powder is less than 0.9%. In an embodiment, the percent silk fibroin (w/w) present in an aqueous solution or powder is less than 0.8%. In an embodiment, the percent silk fibroin (w/w) present in an aqueous solution or powder is less than 0.7%. In an embodiment, the percent silk fibroin (w/w) present in an aqueous solution or powder is less than 0.6%. In an embodiment, the percent silk fibroin (w/w) present in an aqueous solution or powder is less than 0.5%. In an embodiment, the percent silk fibroin (w/w) present in an aqueous solution or powder is less than 0.4%. In an embodiment, the percent silk fibroin (w/w) present in an aqueous solution or powder is less than 0.3%. In an embodiment, the percent silk fibroin (w/w) present in an aqueous solution or powder is less than 0.2%. In an embodiment, the percent silk fibroin (w/w) present in an aqueous solution or powder is less than 0.1%. Higher or lower silk fibroin content may also be possible to suit a particular application, for example, method of application, type of product to be coated, etc.

In some embodiments, the silk fibroin comprises silk fibroin monomers, polymers, and/or fragments. As used herein, the term silk fibroin fragments also include assemblies of silk fibroin fragments. In some embodiments, a silk film and/or coating can be formed from the silk fibroin and the silk film and/or coating comprises a specific percentage (weight/volume) of silk fibroin fragments. In some embodiments, a specific percentage of the silk fibroin fragments have a specific molecular weight (MW). In this context, molecular weight (MW) refers to the molecular weight of individual silk fibroin fragments in a silk film and/or coating, and is not to be confused with weight average molecular weight ($M_w$). To measure the various characteristics of the silk, one could use any industry appropriate method or device. In one example, gel permeation chromatography (GPC) could be used to acquire the molecular weight (MW) of silk fibroin fragments and the weight average molecular weight ($M_w$) of the silk.

As an illustrative example, FIGS. 12 and 13 illustrate two different exemplary graphs of the molecular weights of silk fibroin fragments present in a silk film and/or coating. The X axis represents molecular weight (MW), and the Y axis represents intensity (e.g., the number of silk fibroin fragments with the same molecular weight). The blue bar illustrates a molecular weight (MW) range (e.g., 50 kDa to 100 kDa) that includes a certain percentage (e.g., 10%) of the fibroin fragments in the silk film and/or coating, which is measured when the silk fibroin fragments are still in solution. The Figures also include peaks (P), for example FIG. 12 has one peak and FIG. 13 has two peaks. As a further example, a graph of the molecular weights (MW) of a silk film and/or coating could include more than two peaks. For the purposes of this disclosure, the number of peaks is not limiting and does not impact the percentages of silk fibroin fragments with a specific molecular weight (MW) as discussed herein. Molecular weights may also be measured via other means, such as sodium dodecyl sulphate-polyacrylamide gel electrophoresis (SDS-PAGE) or other similar techniques.

In some aspects, none of the silk fibroin fragments have a molecular weight (MW) under 100 kilodaltons (kDa), less than 1% of the silk fibroin fragments have a molecular weight (MW) under 100 kDa, more than about 1% of the silk fibroin fragments have a molecular weight (MW) under 100 kDa, more than about 5% of the silk fibroin fragments have a molecular weight (MW) under 100 kDa, more than about 10% of the silk fibroin fragments have a molecular weight (MW) under 100 kDa, more than about 15% of the silk fibroin fragments have a molecular weight (MW) under 100 kDa, more than about 20% of the silk fibroin fragments have a molecular weight (MW) under 100 kDa, more than about 25% of the silk fibroin fragments have a molecular weight (MW) under 100 kDa, more than about 30% of the silk fibroin fragments have a molecular weight (MW) under 100 kDa, more than about 35% of the silk fibroin fragments have a molecular weight (MW) under 100 kDa, more than about 40% of the silk fibroin fragments have a molecular weight (MW) under 100 kDa, more than about 45% of the silk fibroin fragments have a molecular weight (MW) under 100 kDa, more than about 50% of the silk fibroin fragments have a molecular weight (MW) under 100 kDa, more than about 55% of the silk fibroin fragments have a molecular weight (MW) under 100 kDa, more than about 60% of the silk fibroin fragments have a molecular weight (MW) under 100 kDa, more than about 65% of the silk fibroin fragments have a molecular weight (MW) under 100 kDa, more than about 70% of the silk fibroin fragments have a molecular weight (MW) under 100 kDa, more than about 75% of the silk fibroin fragments have a molecular weight (MW) under 100 kDa, more than about 80% of the silk fibroin fragments have a molecular weight (MW) under 100 kDa, more than about 85% of the silk fibroin fragments have a molecular weight (MW) under 100 kDa, more than about 90% of the silk fibroin fragments have a molecular weight (MW) under 100 kDa, more than about 95% of the silk fibroin fragments have a molecular weight (MW) under 100 kDa.

In some aspects, none of the silk fibroin fragments have a molecular weight (MW) above 100 kDa, less than 1% of the silk fibroin fragments have a molecular weight (MW) above 100 kDa, more than about 1% of the silk fibroin fragments have a molecular weight (MW) above 100 kDa, more than about 5% of the silk fibroin fragments have a molecular weight (MW) above 100 kDa, more than about 10% of the silk fibroin fragments have a molecular weight (MW) above 100 kDa, more than about 15% of the silk fibroin fragments have a molecular weight (MW) above 100 kDa, more than about 20% of the silk fibroin fragments have a molecular weight (MW) above 100 kDa, more than about 25% of the silk fibroin fragments have a molecular weight (MW) above 100 kDa, more than about 30% of the silk fibroin fragments have a molecular weight (MW) above 100 kDa, more than about 35% of the silk fibroin fragments have a molecular weight (MW) above 100 kDa, more than about 40% of the silk fibroin fragments have a molecular weight (MW) above 100 kDa, more than about 45% of the silk fibroin fragments have a molecular weight (MW) above 100 kDa, more than about 50% of the silk fibroin fragments have a molecular weight (MW) above 100 kDa, more than about 55% of the silk fibroin fragments have a molecular weight (MW) above 100 kDa, more than about 60% of the silk fibroin fragments have a molecular weight (MW) above 100 kDa, more than about 65% of the silk fibroin fragments have a molecular weight (MW) above 100 kDa, more than about 70% of the silk fibroin fragments have a molecular weight (MW) above 100 kDa, more than about 75% of the silk fibroin fragments have a molecular weight (MW) above 100 kDa, more than about 80% of the silk fibroin fragments have a molecular weight (MW) above 100 kDa, more than about 85% of the silk fibroin fragments have a molecular weight (MW) above 100 kDa, more than about 90% of the silk fibroin fragments have a molecular weight (MW) above 100 kDa, more than about 95% of the silk fibroin fragments have a molecular weight (MW) above 100 kDa.

In some aspects, none of the silk fibroin fragments have a molecular weight (MW) above 200 kDa, less than 1% of the silk fibroin fragments have a molecular weight (MW) above 200 kDa, more than about 1% of the silk fibroin fragments have a molecular weight (MW) above 200 kDa, more than about 5% of the silk fibroin fragments have a molecular weight (MW) above 200 kDa, more than about 10% of the silk fibroin fragments have a molecular weight (MW) above 200 kDa, more than about 15% of the silk fibroin fragments have a molecular weight (MW) above 200 kDa, more than about 20% of the silk fibroin fragments have a molecular weight (MW) above 200 kDa, more than about 25% of the silk fibroin fragments have a molecular weight (MW) above 200 kDa, more than about 30% of the silk fibroin fragments have a molecular weight (MW) above 200 kDa, more than about 35% of the silk fibroin fragments have a molecular weight (MW) above 200 kDa, more than about 40% of the silk fibroin fragments have a molecular weight (MW) above 200 kDa, more than about 45% of the silk fibroin fragments have a molecular weight (MW) above 200 kDa, more than about 50% of the silk fibroin fragments have a molecular weight (MW) above 200 kDa, more than about 55% of the silk fibroin fragments have a molecular weight (MW) above 200 kDa, more than about 60% of the silk fibroin fragments have a molecular weight (MW) above 200 kDa, more than about 65% of the silk fibroin fragments have a molecular weight (MW) above 200 kDa, more than about 70% of the silk fibroin fragments have a molecular weight (MW) above 200 kDa, more than about 75% of the silk fibroin fragments have a molecular weight (MW) above 200 kDa, more than about 80% of the silk fibroin fragments have a molecular weight (MW) above 200 kDa, more than about 85% of the silk fibroin fragments have a molecular weight (MW) above 200 kDa, more than about 90% of the silk fibroin fragments have a molecular weight (MW) above 200 kDa, more than about 95% of the silk fibroin fragments have a molecular weight (MW) above 200 kDa.

In some aspects, none of the silk fibroin fragments have a molecular weight (MW) above 300 kDa, less than 1% of the silk fibroin fragments have a molecular weight (MW) above 300 kDa, more than about 1% of the silk fibroin fragments have a molecular weight (MW) above 300 kDa, more than about 5% of the silk fibroin fragments have a molecular weight (MW) above 300 kDa, more than about 10% of the silk fibroin fragments have a molecular weight (MW) above 300 kDa, more than about 15% of the silk fibroin fragments have a molecular weight (MW) above 300 kDa, more than about 20% of the silk fibroin fragments have a molecular weight (MW) above 300 kDa, more than about 25% of the silk fibroin fragments have a molecular weight (MW) above 300 kDa, more than about 30% of the silk fibroin fragments have a molecular weight (MW) above 300 kDa, more than about 35% of the silk fibroin fragments have a molecular weight (MW) above 300 kDa, more than about 40% of the silk fibroin fragments have a molecular weight (MW) above 300 kDa, more than about 45% of the silk fibroin fragments have a molecular weight (MW) above 300 kDa, more than about 50% of the silk fibroin fragments have a molecular weight (MW) above 300 kDa, more than about 55% of the silk fibroin fragments have a molecular weight (MW) above 300 kDa, more than about 60% of the silk fibroin fragments have a molecular weight (MW) above 300 kDa, more than about 65% of the silk fibroin fragments have a molecular weight (MW) above 300 kDa, more than about 70% of the silk fibroin fragments have a molecular weight (MW) above 300 kDa, more than about 75% of the silk fibroin fragments have a molecular weight (MW) above 300 kDa, more than about 80% of the silk fibroin fragments have a molecular weight (MW) above 300 kDa, more than about 85% of the silk fibroin fragments have a molecular weight (MW) above 300 kDa, more than about 90% of the silk fibroin fragments have a molecular weight (MW) above 300 kDa, more than about 95% of the silk fibroin fragments have a molecular weight (MW) above 300 kDa.

In some aspects, none of the silk fibroin fragments have a molecular weight (MW) above 400 kDa, less than 1% of the silk fibroin fragments have a molecular weight (MW) above 400 kDa, more than about 1% of the silk fibroin fragments have a molecular weight (MW) above 400 kDa, more than about 5% of the silk fibroin fragments have a molecular weight (MW) above 400 kDa, more than about 10% of the silk fibroin fragments have a molecular weight (MW) above 400 kDa, more than about 15% of the silk fibroin fragments have a molecular weight (MW) above 400 kDa, more than about 20% of the silk fibroin fragments have a molecular weight (MW) above 400 kDa, more than about 25% of the silk fibroin fragments have a molecular weight (MW) above 400 kDa, more than about 30% of the silk fibroin fragments have a molecular weight (MW) above 400 kDa, more than about 35% of the silk fibroin fragments have a molecular weight (MW) above 400 kDa, more than about 40% of the silk fibroin fragments have a molecular weight (MW) above 400 kDa, more than about 45% of the silk fibroin fragments have a molecular weight (MW) above 400 kDa, more than about 50% of the silk fibroin fragments have a molecular weight (MW) above 400 kDa, more than about 55% of the silk fibroin fragments have a molecular weight (MW) above 400 kDa, more than about 60% of the silk fibroin fragments have a molecular weight (MW) above 400 kDa, more than about 65% of the silk fibroin fragments have a molecular weight (MW) above 400 kDa, more than about 70% of the silk fibroin fragments have a molecular weight (MW) above 400 kDa, more than about 75% of the silk fibroin fragments have a molecular weight (MW) above 400 kDa, more than about 80% of the silk fibroin fragments have a molecular weight (MW) above 400 kDa, more than about 85% of the silk fibroin fragments have a molecular weight (MW) above 400 kDa, more than about 90% of the silk fibroin fragments have a molecular weight (MW) above 400 kDa, more than about 95% of the silk fibroin fragments have a molecular weight (MW) above 400 kDa.

In some aspects, between about 1% and about 10% of the silk fibroin fragments have a molecular weight (MW) under 100 kDa, between about 1% and about 15% of the silk fibroin fragments have a molecular weight (MW) under 100 kDa, between about 1% and about 30% of the silk fibroin fragments have a molecular weight (MW) under 100 kDa, between about 10% and about 30% of the silk fibroin fragments have a molecular weight (MW) under 100 kDa, between about 10% and about 50% of the silk fibroin fragments have a molecular weight (MW) under 100 kDa, between about 10% and about 75% of the silk fibroin fragments have a molecular weight (MW) under 100 kDa, between about 10% and about 95% of the silk fibroin fragments have a molecular weight (MW) under 100 kDa, between about 15% and about 30% of the silk fibroin fragments have a molecular weight (MW) under 100 kDa, between about 15% and about 40% of the silk fibroin fragments have a molecular weight (MW) under 100 kDa, between about 20% and about 30% of the silk fibroin fragments have a molecular weight (MW) under 100 kDa, between about 20% and about 35% of the silk fibroin fragments have a molecular weight (MW) under 100 kDa, between about 30% and about 50% of the silk fibroin fragments have a molecular weight (MW) under 100 kDa, between about 50% and about 90% of the silk fibroin fragments have a molecular weight (MW) under 100 kDa, between about 50% and about 75% of the silk fibroin fragments have a molecular weight (MW) under 100 kDa, between about 60% and about 75% of the silk fibroin fragments have a molecular weight (MW) under 100 kDa, between about 75% and about 95% of the silk fibroin fragments have a molecular weight (MW) under 100 kDa, between about 80% and about 95% of the silk fibroin fragments have a molecular weight (MW) under 100 kDa.

In some aspects, between about 1% and about 90% of the silk fibroin fragments have a molecular weight (MW) above 100 kDa, between about 30% and about 90% of the silk fibroin fragments have a molecular weight (MW) above 100 kDa, between about 40% and about 90% of the silk fibroin fragments have a molecular weight (MW) above 100 kDa, between about 50% and about 90% of the silk fibroin fragments have a molecular weight (MW) above 100 kDa, between about 60% and about 90% of the silk fibroin fragments have a molecular weight (MW) above 100 kDa, between about 50% and about 85% of the silk fibroin fragments have a molecular weight (MW) above 100 kDa, between about 60% and about 85% of the silk fibroin fragments have a molecular weight (MW) above 100 kDa, between about 55% and about 80% of the silk fibroin fragments have a molecular weight (MW) above 100 kDa, between about 65% and about 85% of the silk fibroin fragments have a molecular weight (MW) above 100 kDa, between about 60% and about 80% of the silk fibroin fragments have a molecular weight (MW) above 100 kDa, between about 70% and about 80% of the silk fibroin fragments have a molecular weight (MW) above 100 kDa, between about 60% and about 99% of the silk fibroin fragments have a molecular weight (MW) above 100 kDa, between about 70% and about 99% of the silk fibroin fragments have a molecular weight (MW) above 100 kDa, between about 80% and about 99% of the silk fibroin fragments have a molecular weight (MW) above 100 kDa, between about 90% and about 99% of the silk fibroin fragments have a molecular weight (MW) above 100 kDa.

In some aspects, between about 0.1% and about 40% of the silk fibroin fragments have a molecular weight (MW) above 200 kDa, between about 0.1% and about 30% of the silk fibroin fragments have a molecular weight (MW) above 200 kDa, between about 0.1% and about 20% of the silk fibroin fragments have a molecular weight (MW) above 200 kDa, between about 0.1% and about 10% of the silk fibroin fragments have a molecular weight (MW) above 200 kDa, between about 0.5% and about 40% of the silk fibroin fragments have a molecular weight (MW) above 200 kDa, between about 0.5% and about 30% of the silk fibroin fragments have a molecular weight (MW) above 200 kDa, between about 0.5% and about 20% of the silk fibroin fragments have a molecular weight (MW) above 200 kDa, between about 0.5% and about 10% of the silk fibroin fragments have a molecular weight (MW) above 200 kDa, between about 1% and about 30% of the silk fibroin fragments have a molecular weight (MW) above 200 kDa, between about 1% and about 20% of the silk fibroin fragments have a molecular weight (MW) above 200 kDa, between about 1% and about 10% of the silk fibroin fragments have a molecular weight (MW) above 200 kDa, between about 20% and about 80% of the silk fibroin fragments have a molecular weight (MW) above 200 kDa, between about 40% and about 90% of the silk fibroin fragments have a molecular weight (MW) above 200 kDa, between about 50% and about 90% of the silk fibroin fragments have a molecular weight (MW) above 200 kDa, between about 60% and about 90% of the silk fibroin fragments have a molecular weight (MW) above 200 kDa, between about 60% and about 80% of the silk fibroin fragments have a molecular weight (MW) above 200 kDa.

In some aspects, between about 0.1% and about 3% of the silk fibroin fragments have a molecular weight (MW) above 300 kDa, between about 0.1% and about 5% of the silk fibroin fragments have a molecular weight (MW) above 300 kDa, between about 0.1% and about 10% of the silk fibroin fragments have a molecular weight (MW) above 300 kDa, between about 1% and about 30% of the silk fibroin fragments have a molecular weight (MW) above 300 kDa, between about 1% and about 10% of the silk fibroin fragments have a molecular weight (MW) above 300 kDa, between about 1% and about 20% of the silk fibroin fragments have a molecular weight (MW) above 300 kDa, between about 5% and about 20% of the silk fibroin fragments have a molecular weight (MW) above 300 kDa, between about 10% and about 20% of the silk fibroin fragments have a molecular weight (MW) above 300 kDa, between about 10% and about 30% of the silk fibroin fragments have a molecular weight (MW) above 300 kDa, between about 10% and about 50% of the silk fibroin fragments have a molecular weight (MW) above 300 kDa, between about 10% and about 75% of the silk fibroin fragments have a molecular weight (MW) above 300 kDa, between about 10% and about 95% of the silk fibroin fragments have a molecular weight (MW) above 300 kDa, between about 15% and about 30% of the silk fibroin fragments have a molecular weight (MW) above 300 kDa, between about 20% and about 50% of the silk fibroin fragments have a molecular weight (MW) above 300 kDa, between about 30% and about 50% of the silk fibroin fragments have a molecular weight (MW) above 300 kDa, between about 50% and about 90% of the silk fibroin fragments have a molecular weight (MW) above 300 kDa, between about 50% and about 75% of the silk fibroin fragments have a molecular weight (MW) above 300 kDa, between about 60% and about 75% of the silk fibroin fragments have a molecular weight (MW) above 300 kDa, between about 75% and about 95% of the silk fibroin fragments have a molecular weight (MW) above 300 kDa, between about 80% and about 95% of the silk fibroin fragments have a molecular weight (MW) above 300 kDa.

In some aspects, between about 1% and about 5% of the silk fibroin fragments have a molecular weight (MW) above 400 kDa, between about 1% and about 10% of the silk fibroin fragments have a molecular weight (MW) above 400 kDa, between about 1% and about 20% of the silk fibroin fragments have a molecular weight (MW) above 400 kDa, between about 1% and about 30% of the silk fibroin fragments have a molecular weight (MW) above 400 kDa, between about 1% and about 60% of the silk fibroin fragments have a molecular weight (MW) above 400 kDa, between about 5% and about 10% of the silk fibroin fragments have a molecular weight (MW) above 400 kDa, between about 5% and about 15% of the silk fibroin fragments have a molecular weight (MW) above 400 kDa, between about 5% and about 20% of the silk fibroin fragments have a molecular weight (MW) above 400 kDa, between about 30% and about 60% of the silk fibroin fragments have a molecular weight (MW) above 400 kDa, between about 35% and about 55% of the silk fibroin fragments have a molecular weight (MW) above 400 kDa, between about 35% and about 75% of the silk fibroin fragments have a molecular weight (MW) above 400 kDa, between about 35% and about 85% of the silk fibroin fragments have a molecular weight (MW) above 400 kDa, between about 50% and about 85% of the silk fibroin fragments have a molecular weight (MW) above 400 kDa, between about 55% and about 80% of the silk fibroin fragments have a molecular weight (MW) above 400 kDa, between about 70% and about 90% of the silk fibroin fragments have a molecular weight (MW) above 400 kDa.

In one aspect, the disclosure relates to a silk manufacturing system including multiple processing substations. Specifically, the system includes a first processing substation with a vessel configured to receive silkworm cocoons and extract silk fibroin proteins therefrom to produce a silk fibroin-based solution, a second processing substation in fluid communication with the first processing substation and configured to receive and purify the silk fibroin-based solution from the first processing substation, a third processing substation in fluid communication with the second processing substation and configured to receive and sterilize the purified silk fibroin-based solution, and a fourth processing substation in fluid communication with the third processing substation and configured to receive and powderize the silk fibroin-based solution. In various aspects, the systems disclosed herein may include any number and arrangement of processing substations as necessary for a particular application.

In various embodiments of the foregoing aspect, the system further includes a pump assembly disposed between the first and second processing substations and configured to transfer the silk fibroin-based solution from the first processing substation to the second processing substation. The system may also include a reservoir disposed between the first and second processing substations and configured to at least one of hold or condition the silk fibroin-based solution, such as, for example, to adjust a temperature of the solution or adjust a concentration of one or more components of the solution. Additionally, the system may further include a filtration system disposed between the first and second processing substations and configured to filter the silk fibroin-based solution and a heat exchange system configured to adjust a temperature of the silk fibroin-based solution prior to or after any one of the processing substations.

In further embodiments, the first processing substation is configured to extract the silk fibroin proteins via degumming, rinsing, and dissolving processes within a single vessel. The second processing substation may be configured to purify the silk fibroin-based solution and/or concentrate the silk fibroin-based solution to have a higher percentage of silk fibroin via ultrafiltration and/or diafiltration, with or without the use of tangential flow filtration, or dialysis. The third processing substation may be configured to moderately clean or sterilize the purified silk fibroin-based solution via one or more of ultrafiltration, microfiltration, pasteurization, or something similar. Generally, sterilization is not necessarily intended to include a solution completely free from bacteria or other living microorganisms, but it could be. Another substation may be centrifugation or microfiltration to reduce turbidity. Excess turbidity may be undesirable in a silk fibroin-based solution, as it may impact the tackiness of a coating made from the silk fibroin-based solution, hinder the barrier forming properties of the silk solution, and/or may cause a coating formed from the silk fibroin-based solution to look cloudy or milky. For this reason, turbidity may be kept under about 1.000 optical density, including in solution concentrations of 2.5%, 5%, 7.5, 10%, 12.5%, 15%, 17.5%, or 20% silk fibroin-in-water, wherein the optical density is measured at a wavelength of 660 nm (OD660). In some embodiments, the turbidity may be kept under a lower limit, such as about 0.900, 0.800, 0.700, 0.600, 0.500, 0.400, 0.300, 0.200, 0.100, 0.050 (OD600), or in any increments within.

Additionally, the presence of excessive amounts of microbes may negatively impact the performance of the silk solution and potentially make the silk fibroin-based solution unfit for human consumption or target application, including in pre-harvest applications, post-harvest applications, animal-feed applications, or other such applications. For this reason, microbes should be killed and/or substantially removed from the silk fibroin-based solution, which may range from a small level of reduction to essentially complete removal as, for example, may be determined within the limitations of detection and/or the type of microbes (e.g., under 100, 90, 80, 70, 60, 50, 40, 30, 20, or 10 cfu/g for mold, yeast, Enterobacteriaceae, *Staphylococcus aureus*, *Escherichia coli*, and a "Negative/under 25 g" reading for *Salmonella* and *Listeria monocytogenes*). In one example, this may mean keeping the amounts of microbes under 10 CFU/ml under any acceptable testing mechanism, for example total aerobic plate count on plate count agar (PCA) and/or potato dextrose agar (PDA). In some cases, the third processing substation is configured to sterilize the purified silk fibroin-based solution to a food grade standard. In some cases, the third processing substation may be removed entirely from the system. In those cases, or other cases, the previous substations may produce a food grade standard product and/or sterilize the silk-fibroin based solution to the level discussed herein. For example, the first substation may sterilize the silk-fibroin based solution by treating the silk fibroin-based solution at a certain temperature to remove microbes from the solution. In this example, the entire system could alternatively be closed, so that no further sterilization is necessary. In other cases, the third processing substation may be placed at different locations in the system. In some cases, the entire system may be a closed system such that microbes may not be present in large enough numbers to necessitate the third processing substation. Furthermore, the fourth processing substation may be configured to powderize the purified silk fibroin-based solution via spray drying, freeze drying, or similar drying and powderization methods known in the industry.

In still other embodiments, the system may further include a pre-treatment system configured to condition the silkworm cocoons prior to or at introduction to the first processing substation, such as, for example, a shredder for shredding the silkworm cocoons, softening equipment, soaking equipment, and/or material handling equipment. In some embodiments, the silkworm cocoons are shredded to a reduced size and shape (e.g., 0.5-50 cm fragments or 0.5-50 cm strands of longer silk floss, sheets, or wadding) and/or treated or pressed. In some embodiments, prior to introduction into the system, the cocoons or other silk inputs may be stripped of sericin, washed to remove organic and inorganic compounds, stripped of other proteins, or combined with more than one silk input to increase the amount of fibroin per unit mass of silk input. This may or may not include shredding or cutting or a preliminary degum step. In addition, the pretreatment equipment may include systems for cleaning the cocoons, including separating debris from the cocoons, testing the cocoons (e.g., chemical analysis), and/or performing other quality control processes, including cocoon composition assessments.

The system may also include a post-treatment system configured to receive the silk fibroin powder from the fourth processing substation. The post-treatment equipment may include equipment conditioning the silk fibroin powder by the addition of one or more additives or silk powder from a different batch with different chemical or polymer characteristics (i.e., molecular weight profiles, turbidities, or the like) (e.g., lower molecular weight silk fibroin may be added to higher molecular weight silk fibroin to allow for an increase in instantization and solubility or to allow for different characteristics and properties). The post-treatment equipment may also add a heat treatment step or an agglomeration step that may make the powder dryer, wetter, denser, cleaner, and/or more instantizable. The post-treatment equipment may also include equipment for testing the silk fibroin powder and/or packaging the silk fibroin powder. The post-treatment step may be an aseptic method of packaging to allow for shelf-stable silk fibroin powder.

The system may include a controller in communication with the various processing substations (e.g., valve assemblies, sensors, switches, transmitters, drives, etc.) and configured to control one or more of the introduction variables (e.g., volumes, flow rates, mixing rates, agitation speeds, timing/duration of a process, pre-processing operations, component proportions, pH levels, temperatures, pressures, solution amounts, solids amounts, etc.) of the various components (e.g., cocoons, solvents, compounds, etc.), controlling a degumming operation (e.g., soak times and temperatures, pressurization, agitation speeds and timing thereof, volume control (i.e., draining and refilling vessel, recirculation)), controlling a rinse operation (e.g., determining state of solution, draining and refilling of the vessel, addition of a solvent, frequency and duration of the various steps, pressurization, or depressurization), controlling the silk fibroin dissolving operation (e.g., addition of the second compound and concentration thereof, time, temperature, pressure, agitation speeds and timing thereof, duration, etc.), controlling outputs from the substations (e.g., flow rates, temperatures, etc.).

In various embodiments of any of the aspects disclosed herein, the first processing substation includes a reactor vessel having a first inlet port configured to receive the silkworm cocoons and one or more ingredients (e.g., soda ash, a chaotropic agent, a catalyst, additive, or similar), a second inlet port configured to receive a solvent (e.g., water, ethanol, citric acid, etc.) and at least one outlet configured to output the silk fibroin-based solution. The reactor vessel is configured to process the silkworm cocoons by at least one of degumming, rinsing, and dissolving the silk fibroin protein from the cocoons. The first processing substation may also include a water or oil jacket disposed about the reactor vessel that is configured to provide heat exchange (e.g., heating or cooling as necessary) with the vessel and its contents. The first processing substation may further include equipment configured to agitate the contents of the reactor vessel, such as, for example, a mixer, a vibration plate, a magnetic stirrer, sonicator, liquid pumps, air pumps, aqueous streams, etc. The agitation may occur through pressure streams external or internal, where the pressure streams are liquid and/or gasses. In various embodiments, the agitation equipment may be disposed proximate a bottom or top surface of the reactor vessel. In various embodiments, the agitation equipment may be disposed in various portions of the reactor vessel (i.e., pumps at the bottom, center, and top; agitator at the bottom and pump at the top; etc.). In some embodiments, the agitation equipment is a mixer having a unitary shaft and impeller. The impeller may be configured for axial flow, radial flow, and/or tangential flow, and may be run in reverse. Additionally, the impeller may be coated with a substance to resist attachment of silk fibers and/or have a surface finish of the blades (e.g., a surface roughness below some threshold value). The mixer may have interchangeable impellers, where the impellers may be configured to suit particular processes and have one or more of flat blades, curved blades, pitched blades, finger blades, anchor blades, gate blades, ribbon blades, etc. having different shapes, pitch, etc. The impeller may also be configured to be raised and lowered into the vessel or within the vessel contents during or between different processing steps.

In further embodiments, the reactor vessel includes a second outlet for removing at least a portion of the solvent and any residue therein (e.g., dissolved sericin), which can be sent to waste, recirculated, or recycled. The reactor vessel may have a glass lining and be sized to have an aspect ratio of 0.5-5.0, or more preferably 0.8-2, and more preferably 1.0-1.5 of height to diameter as defined by a work volume. The aspect ratio may be selected to suit a particular application, for example, temperature control, processing rates, desired volumes, work space, etc. The volume of the vessel will vary to suit a particular application (e.g., finished yields) and may range from about 0.25 liters to about 80,000 liters depending on the batch size required, preferably 0.5 liters to 5,000 liters. Additionally, the reactor vessel may have shapes other than cylindrical, such that the aspect ratio will be the vessel height to cross-sectional area (e.g., rectangular, ovoid, etc. cross-sectional shapes) thereof. The vessel contents may include a plurality of silkworm cocoons (with or without pre-treatment), a solvent (e.g., water), and a compound. The packing density of the silkworm cocoons will vary to suit a particular application (e.g., finished silk fibroin-based solution) and/or different silk inputs (e.g., cocoons, floss, etc.) and may range from: about 1%-100%, about 1%-70%, about 1%-50%, about 1%-30%, about 1%-20%, about 2%-20%, about 2%-15%, less than about 100%, less than about 90%, less than about 80%, less than about 70%, less than about 60%, less than about 50%, less than about 40%, less than about 30%, less than about 25%, less than about 20%, less than about 15%, less than about 10%, less than about 5%, greater than about 1%, greater than about 5%, greater than about 10%, greater than about 15%, greater than about 20%, greater than about 30%, greater than about 40%, greater than about 50%, greater than about 60%, greater than about 70%, greater than about 80%, greater than about 90%. The water or oil jacket is configured to heat the contents to a temperature of about 50° C. to about 150° C., preferably about 75° C. to about 125° C., or other temperature to suit a particular application. In addition, the rinse step may include performing 1 to 30 rinse cycles, more preferably about 1 to about 10 rinse cycles, more preferably about 3 to about 10 rinse cycles, and more preferably about 4 to about 6 rinse cycles, or essentially any number of rinse cycles to suit a particular application. Generally, the process times, temperatures, pH, and other solution characteristics may vary to suit a particular application, such as the type of silk, or a particular output specification.

The reactor vessel may also include a handling structure or equipment configured to control the movement and/or the position of the silkworm cocoons within the vessel (e.g., prevent floating of the cocoons). The equipment may include, for example, a screen or netting disposed proximate a lower portion of the vessel and configured to separate the silkworm cocoons from the agitation equipment and/or prevent the silkworm cocoons from floating to the top of the vessel, a chute or funnel structure in communication with the first inlet and configured to direct the silkworm cocoons to a particular location within the vessel during introduction thereof, a recirculation system configured to draw a portion of the solution from a lower portion of the vessel and reintroduce the solution to an upper portion of the vessel and/or introduce fresh water to push the silkworm cocoons down into the solution, a vertically movable sieve (e.g., a perforated plunger) disposed within the vessel and configured to "push" any solids within the solution towards a lower portion of the vessel, and one or more baffles disposed within the vessel and extending from an inner wall thereof, where the baffles direct the movement of the solution and contents therein. In some embodiments, the movement of the silkworm cocoons may be controlled by adjusting the processing temperatures during various stages of the process. For example, during a degumming operation, the contents may be heated to a temperature slightly lower than their boiling point to reduce the formation of air bubbles. Other manners of controlling movement of the cocoons are described in greater detail below. See, for example, FIGS. 9-11.

The first processing substation, and system generally, may include one or more valve assemblies (with manual or automatic actuators) that are configured to control the introduction and removal from the first processing substation and/or the reactor vessel of any component, such as, for example, silkworm cocoons, compounds, solvents, waste solutions, residues, and final silk fibroin-based solutions. The first processing substation, and system generally, may include at least one sensor configured to sense one or more of solution temperatures, concentrations, flow rates, pH, fluid levels, turbidity, particle size, molecular weight, pressurization, etc., which may be used to control (with or without human intervention) the operation of the various processes.

In further embodiments of any of the aspects disclosed herein, the second processing substation includes a filtration module housing at least one membrane. The filtration module has an inlet configured to receive the silk fibroin-based solution including a second compound (e.g., a chaotropic agent, such as: calcium bromide; magnesium chloride; lithium acetate; lithium perchlorate; guanidinium chloride; ethanol; methanol; urea; thiourea; sodium dodecyl sulfate; lithium thiocyanate (LiSCN); sodium thiocyanate (NaSCN); calcium thiocyanate ($Ca(SCN)_2$); magnesium thiocyanate ($Mg(SCN)_2$); anhydrous or dihydrate calcium chloride (CaCl2); lithium chloride (LiCl); lithium bromide (LiBr); zinc chloride ($ZnCl_2$); copper nitrate ($Cu(NO_2)_2$); copper ethylene diamine ($Cu(NH_2CH_2CH_2NH_2)_2(OH)_2$); $Cu(NH_3)_4$ $(OH)_2$; Ajisawa's reagent ($CaCl_2$/ethanol/water); isopropanol; 1-butanol; 2-butanol; ethyl acetate; calcium nitrate; magnesium nitrate; calcium perchlorate; calcium chlorate; calcium acetate; dicalcium phosphate/calcium hydrogen phosphate; calcium sulfate; calcium fluoride; ammonium fluoride; ammonium sulfate; ammonium phosphate; diammonium phosphate (diammonium hydrogen phosphate); ammonium dihydrogen phosphate; ammonium acetate; ammonium chloride; ammonium bromide; ammonium nitrate; ammonium chlorate; ammonium iodide; ammonium perchlorate; ammonium thiocyanate; potassium fluoride; potassium sulfate; monopotassium phosphate; dipotassium phosphate (potassium hydrogen phosphate); tripotassium phosphate; potassium acetate; potassium chloride; potassium bromide; potassium nitrate; potassium chlorate; potassium iodide; potassium perchlorate; potassium thiocyanate; sodium fluoride; sodium sulfate; sodium monophosphates (e.g., monosodium phosphate, disodium phosphate, trisodium phosphate); sodium di- and polyphosphates (e.g., monosodium diphosphate, disodium diphosphate, tri sodium diphosphate, tetrasodium diphosphate, sodium triphosphate); sodium acetate; sodium chloride; sodium bromide; sodium nitrate; sodium chlorate; sodium iodide; sodium perchlorate; lithium fluoride; lithium sulfate; lithium phosphate; lithium chloride; lithium bromide; lithium nitrate; lithium chlorate; lithium iodide; magnesium fluoride; magnesium sulfate; monomagnesium phosphate; mimagnesium phosphate; trimagnesium phosphate; magnesium acetate; magnesium bromide; magnesium chlorate; magnesium iodide; magnesium perchlorate; magnesium thiocyanate; monocalcium phosphate; tricalcium phosphate; octacalcium phosphate; dicalcium diphosphate; calcium triphosphate; calcium iodide; guanidinium nitrate; guanidinium iodide; guanidinium thiocyanate, or a combination thereof), an outlet configured to output a purified silk fibroin-based solution with a reduced concentration of any chaotropic agent (i.e., the retentate), and a waste port configured to output a portion of the second compound (i.e., the permeate). The filtration module is configured to remove the second compound from the silk fibroin-based solution via diafiltration or dialysis. In some cases, the flow through the module is tangential to a surface of the membrane. The silk fibroin-based solution may also experience some level of concentration that may be tuned to optimize a later process (e.g., sterilization or powderization). The silk fibroin-based solution may be circulated through the filtration module for a duration defined by about 1 diavolumes to about at least 12 diavolumes, preferably about 3 diavolumes to about 10 diavolumes, and more preferably about 5 diavolumes to about 9 diavolumes. In some cases, the concentrations levels of the chaotropic agent in the retentate and/or the pressure drop across the filtration module may also be monitored to determine a state of the process. Generally, it is desirable to obtain a level of remaining chaotropic agent that is virtually undetectable to a user (e.g., tasteless); however, this level will vary for different agents and/or product applications and may include less than 1,000 parts per million (ppm), less than 900 ppm, less than 650 ppm, less than 400 ppm, less than 300 ppm, less than 250 ppm, and even as low as under 150 ppm. In some cases, other tests are conducted to ensure that no contaminants or unwanted materials are present in the silk fibroin-based solution.

Additionally, the filtration module may include one or more spiral wound membranes; however, other membrane structures, such as plate and frame, hollow fiber, etc., may be used to suit a particular application (e.g., flow rates, pressures, etc.). The filtration module may include multiple stages and may include about one to about ten membranes, about one to about eight membranes, about three to about eight membranes, about three to about five membranes. Where multiple filter stages or filtration modules are used, the silk fibroin-based solution may pass therethrough in series, parallel, or both to suit a particular application. The number, size, and configuration of the membranes will be selected based on the various system parameters (e.g., flow rates). The structures and chemistries of the membrane active layers will also vary to suit a particular application and may be structured with a molecular weight cut-off of about 1 kDa to about 300 kDa, about 1 kDa to about 100 kDa, about 1 kDa to about 50 kDa. Additionally, the membranes may be manufactured from polyether sulfone (PES), polyvinylidene fluoride (PVDF), polyacrylonitrile (PAN), polypropylene (PP), polyethylene terephthalate (PET), or combinations thereof.

The second processing substation may also include a heat exchange system, including any valves, pumps, controls, etc. as needed to control a temperature of the silk fibroin-based solution during processing. For example, lowering the temperature of the silk fibroin-based solution prior to introduction to the filtration module may enhance the removal of the second compound. The second processing substation may also include one or more valve assemblies configured to direct the silk fibroin-based solution output with a reduced second compound to at least one of the inlet (recirculation) or to the third processing substation and one or more sensors (e.g., differential pressure, temperatures, flow rates, a salinometer, conductivity, etc.) in communication with the controller. In some embodiments, the filtration module may include a recycling circuit for recovering the removed second compound, such as by evaporation.

In additional embodiments of any of the aspects disclosed herein, the third processing substation includes a microfiltration module having an inlet configured to receive the purified silk fibroin-based solution from the second processing substation and an outlet configured to output a sterile silk fibroin-based solution. The microfiltration module is configured to reduce turbidity and/or remove microbes from the purified silk fibroin-based solution. In some embodiments, the inlet is configured to receive the silk fibroin-based solution from the first processing substation and the outlet is configured to output a sterile silk fibroin-based solution to the second processing substation. Additionally, the microfiltration module may include one or more filter stages, with or without pumps, valves, and holding tanks as necessary. In some embodiments, the first filter stage may be disposed upstream of the second processing substation and the second filter stage may be disposed downstream of the second processing substation. In embodiments including one or more pumps, the pumps are configured to transfer the silk fibroin-based solution between filter stages and/or processing substations and/or to another process as necessary after completing the microfiltration process. In addition, one or more holding tanks may be included to store the solution or provide additional processing, such as temperature control or concentration adjustment, as may be necessary to address turbidity or sterility levels.

The filter stages may include one or more spiral wound membranes; however, other membrane structures, such as plate and frame, hollow fiber, bag filters, cartridges, etc., may be used to suit a particular application. In some embodiments, the microfiltration module may include two (2) stages, where the first stage is configured to remove large aggregates, while the second stage is configured to remove smaller aggregates, and/or to sterilize and reduce the turbidity of the solution. The membranes in the first stage may be configured for depth or surface filtration, with a pore size ranging from 0.65-15 um. The membranes in the second stage may be configured for depth or surface filtration, with a pore size ranging from about 0.05-0.65 µm. The membranes may be made from PES, PP, or cellulose, with or without a food grade filtering aid. The filter stages may include about 1 to about 52 membranes.

The silk fibroin-based solution may pass through the membranes in series, parallel, or both to suit a particular application. The membranes may have an average pore size of about 0.02 µm to about 15 µm. In some embodiments, the membranes in a first filter stage may have a pore size in the range of about 0.7 µm to about 5 µm, preferably about 0.9 µm and about 1.4 µm, while the membranes in a second filter stage may have a pore size in the range of about 0.05 µm to about 0.8 µm, preferably about 0.2 µm to about 0.8 µm, where the silk fibroin-based solution passes through the first filter stage prior to passing through the second filter stage (e.g., to filter out larger aggregates in the first stage). In some cases, the silk fibroin-based solution contains minimal amounts of a chaotropic agent. Additionally, or alternatively, the third processing substation may include a heat exchange circuit to sterilize the solution via pasteurization.

In still further embodiments of any of the aspects disclosed herein, the fourth processing substation includes powderization equipment configured to receive the sterilized silk fibroin-based solution from the third processing substation and output the silk fibroin protein in a powder form. In addition, the resulting powdered silk fibroin may have a water activity level below 1.0, 0.95, 0.9, 0.85, 0.8, 0.75, 0.7, 0.6, 0.5, 0.4, 0.3, 0.2, 0.1. Preferably, the water activity level is under 0.9 to allow for a shelf-stable powder from a food and microbiological standpoint. The powderization equipment may include a spray dryer having an inlet configured to receive the sterilized silk fibroin-based solution from the third processing substation and an outlet configured to output the silk fibroin protein in a powdered and easily instantizable form. In one embodiment, a spray dryer may be configured to have a high pressure nozzle, where the spray is created by forcing feed, in this case silk fibroin-based solution, through a nozzle orifice. Alternatively, a two-fluid nozzle spray dryer may be used, where the spray is created by the interaction between the feed and compressed air. In a two-fluid nozzle configuration, the feed may be atomized via contact with compressed air with or without a subsequent nozzle heating step. Hot drying gases may also be used to accelerate the atomization engine when it meets the feed. The hot drying gases may be configured to travel at a low velocity. Other spray dryer configurations may be also used. As a non-limiting example, the spray dryer may be one of the following types: high pressure nozzle, two-fluid nozzle, combustion nozzle, atomization.

Instantizable may encompass a range of characteristics, including but not limited to a powder that is flowable and easily dispersible in a liquid to form a stable dispersion in the liquid without stirring or shaking the powder in the liquid, but that could alternatively be created by stirring or shaking the powder in the liquid for only a short period of time. In one embodiment, the moisture content of the powder should be between about 1%-10%, more preferably between about 1.0%-7%. The fourth processing substation may also include a feed vessel for holding the sterilized silk fibroin-based solution prior to processing. The feed vessel may be configured treat the sterilized silk fibroin-based solution prior to processing to, for example, enhance powderization or produce a more instantizable powder. The fourth processing substation may also include equipment disposed downstream of the powderization equipment for modifying the powdered silk fibroin protein (e.g., inclusion of an additive to make it more instantizable, or equipment to assist with agglomeration) or packaging equipment. As an example of agglomeration equipment, the fourth processing substation may include an external fluid bed or a fluid bed integrated with the powderization equipment. The agglomeration equipment may aid in agglomeration of the powdered silk fibroin protein, which may improve dispersibility, instantization, or wettability properties of the powdered silk fibroin protein. Any suitable agglomeration equipment may be utilized. In some embodiments, the powdered silk fibroin may be passed through the agglomeration equipment after it is powderized. In other embodiments, the agglomeration equipment may be integrated into the spray dryer such that agglomeration occurs during the powderization process. In some embodiments, the agglomeration equipment may increase the size of the powdered silk fibroin protein particles by more than about 5%, more than about 10%, more than about 20%, more than about 30%, more than about 40%, more than about 50%, more than about 60%, more than about 70%, more than about 80%, more than about 90%, more than about 100%, more than about 150%, more than about 200%, more than about 250%, more than about 300%, more than about 350%, more than about 400%, more than about 500%, more than about 600%, more than about 700%, more than about 800%, more than about 900%, more than about 1000%.

In another aspect, the disclosure relates to a method of processing silkworm cocoons to obtain food grade silk fibroin. The method includes the steps of introducing a plurality of silkworm cocoons to a reactor vessel, introducing a solvent (e.g., water (e.g., softened water, filtered water, deionized water, tap water), ethanol, citric acid, or other suitable substances with an acidic pH) to the reactor vessel, introducing a first compound to the reactor vessel, introducing heat to the contents of the reactor vessel to promote degumming of the silkworm cocoons, optionally pressurizing the reactor vessel and/or optionally agitating the contents of the reactor vessel to control movement of the silkworm cocoons within the reactor vessel, removing at least a portion of the solvent and any degumming residue if any, rinsing the degummed silk fibroin, introducing a second compound to the reactor vessel (with or without additional solvent) to dissolve the remaining silk fibroin proteins in to the solution, filtering the contents of the reactor vessel to substantially remove the second compound (e.g., as necessary to meet a specific level or range of purity) and produce a purified silk fibroin-based solution, directing the purified silk fibroin-based solution to a sterilization process to obtain a "food grade" quality silk fibroin-based solution, and powderizing the purified silk fibroin-based solution to obtain the silk fibroin in a powder form. Various parameters of the process will vary to suit a particular application, for example, the order of, quantities, and rates of introduction or removal of various components (e.g., silkworm cocoons, solvent, compounds, rinse solutions, etc.), operating temperature ranges, processing times (e.g., speed and timing of agitation step(s)), order of operation, etc. In various embodiments, the methods disclosed herein may incorporate any of the additional processes or steps that correspond to the systems and substations disclosed herein.

Embodiment 1: A silk manufacturing system comprising (A) a first processing substation comprising a vessel configured to receive silk inputs, extract silk fibroin proteins therefrom, and produce a silk fibroin-based solution, such that the silk fibroin-based solution is substantially free of sericin, wherein the first processing substation is configured to extract the silk fibroin proteins via degumming, rinsing, and dissolving processes within a single vessel; (B) a second processing substation in fluid communication with the first processing substation, the second processing substation configured to receive and purify the silk fibroin-based solution from the first processing substation, wherein the purified silk fibroin-based solution comprises less than about 650 parts per million (ppm) of one or more salts or non-organic particulates; (C) wherein the silk fibroin-based solution is sterilized to produce a sterilized silk fibroin-based solution prior to a third processing substation; and (D) a third processing substation in fluid communication with the second processing substation, the third processing substation is a spray dyer that is configured to receive and powderize the sterilized silk fibroin-based solution.

Embodiment 2: A silk manufacturing system comprising (A) a first processing substation comprising a vessel configured to receive silk inputs, extract silk fibroin proteins therefrom, and produce a silk fibroin-based solution, wherein the first processing substation is configured to extract the silk fibroin proteins via degumming, rinsing, and dissolving processes within a single vessel; (B) a second processing substation in fluid communication with the first processing substation, the second processing substation configured to receive and purify the silk fibroin-based solution from the first processing substation; (C) a third processing substation in fluid communication with the second processing substation, the third processing substation configured to receive and sterilize the purified silk fibroin-based solution; and (D) a fourth processing substation in fluid communication with the third processing substation, the fourth processing substation configured to receive and powderize the purified silk fibroin-based solution, wherein the fourth processing substation is a spray dryer.

Embodiment 3: A silk manufacturing system comprising (A) a first processing substation configured to receive silk inputs, extract silk fibroin proteins therefrom, and produce a silk fibroin-based solution, wherein the first processing substation is configured to extract the silk fibroin proteins within a single vessel, the first processing substation comprising a reactor vessel comprising a first inlet port configured to receive the raw silk inputs and one or more compounds, a second inlet port configured to receive a solvent, and at least one outlet configured to output the silk fibroin-based solution, wherein the reactor vessel is configured to process the silk inputs by degumming, rinsing, and dissolving the silk fibroin protein from the silk inputs, a liquid jacket disposed about the reactor vessel and configured to provide heat exchange with the vessel and its contents, wherein the liquid jacket is configured to heat the contents to a temperature of about 50° C. to about 150° C., and an agitation mechanism configured to agitate the contents of the reactor vessel; (B) a second processing substation in fluid communication with the first processing substation, the second processing substation configured to receive and purify the silk fibroin-based solution from the first processing substation, wherein the second processing substation is configured to purify the silk fibroin-based solution via tangential flow filtration, the second processing substation comprising a filtration module housing at least one membrane, the module comprising an inlet configured to receive the silk fibroin-based solution including a compound, an outlet configured to output a purified silk fibroin-based solution with a reduced compound amount, and a waste port configured to output a portion of the compound, wherein the filtration module is configured to remove the compound from the silk fibroin-based solution by circulating the silk fibroin-based solution through the filtration module until about 1 diavolume to about at least 12 diavolumes are reached; (C) wherein the silk fibroin-based solution is sterilized to produce a sterilized silk fibroin-based solution prior to a third processing substation; (D) the third processing substation in fluid communication with the second processing substation, the third processing substation configured to receive and powderize the sterilized silk fibroin-based solution, wherein the third processing substation is configured to powderize the sterilized silk fibroin-based solution via a spray dryer, and wherein the third process substation includes a piece of agglomeration equipment; and (E) a post-treatment system configured to receive a silk fibroin powder from the third processing substation and to at least one of: condition the silk fibroin powder, test the silk fibroin powder, or package the silk fibroin powder in a food-safe container.

Embodiment 4: A silk manufacturing system comprising a first processing substation comprising a vessel configured to receive silk inputs, extract silk fibroin proteins therefrom, and produce a silk fibroin-based solution, such that the silk fibroin-based solution is substantially free of sericin, wherein the first processing substation is configured to extract the silk fibroin proteins via degumming, rinsing, and dissolving processes within a single vessel.

Embodiment 5: The silk manufacturing system of any one of Embodiments 1 to 4, or any combination thereof, wherein the purified silk fibroin-based solution comprises less than about 400 ppm of the one or more salts or non-organic particulates.

Embodiment 6: The silk manufacturing system of any one of Embodiments 1 to 5, or any combination thereof, wherein the powderized silk fibroin-based solution comprises a water activity level of less than 0.9.

Embodiment 7: The silk manufacturing system of any one of Embodiments 1 to 6, or any combination thereof, wherein the silk inputs come from a *Bombyx mori* silkworm.

Embodiment 8: The silk manufacturing system of any one of Embodiments 1 to 7, or any combination thereof, further comprising a reservoir disposed between the first and second processing substations and configured to at least one of hold or condition the silk fibroin-based solution and a pump assembly disposed between the first and second processing substations and configured to transfer the silk fibroin-based solution between the first processing substation, the reservoir, and the second processing substation.

Embodiment 9: The silk manufacturing system of any one of Embodiments 1 to 8, or any combination thereof, wherein the second processing substation includes at least one spiral wound filtration membrane.

Embodiment 10: The silk manufacturing system of any one of Embodiments 1 to 9, or any combination thereof, further comprising a heat exchange system configured to adjust a temperature of the silk fibroin-based solution prior to or after any one of the processing substations.

Embodiment 11: The silk manufacturing system of any one of Embodiments 1 to 10, or any combination thereof, wherein the second processing substation is configured to purify the silk fibroin-based solution via diafiltration.

Embodiment 12: The silk manufacturing system of any one of Embodiments 1 to 11, or any combination thereof, wherein the second processing substation is configured to purify the silk fibroin-based solution via tangential flow filtration.

Embodiment 13: The silk manufacturing system of any one of Embodiments 1 to 12, or any combination thereof, wherein the third or fourth processing substation includes a piece of agglomeration equipment.

Embodiment 14: The silk manufacturing system of any one of Embodiments 1 to 13, or any combination thereof, further comprising a post-treatment system configured to receive a silk fibroin powder from the third processing substation and to at least one of: condition the silk fibroin powder, test the silk fibroin powder, or package the silk fibroin powder in a food-safe container.

Embodiment 15: The silk manufacturing system of any one of Embodiments 1 to 14 or any combination thereof, wherein the third processing substation is configured to sterilize the purified silk fibroin-based solution to a food grade standard via microfiltration.

Embodiment 16: The silk manufacturing system of any one of Embodiments 1 to 15 or any combination thereof, wherein the third processing substation is configured to sterilize the purified silk fibroin-based solution to a food grade standard via pasteurization.

Embodiment 17: The silk manufacturing system of any one of Embodiments 1 to 16 or any combination thereof, further comprising a fourth processing substation in fluid communication with the second processing substation, the fourth processing substation configured to receive and sterilize the purified silk fibroin-based solution.

Embodiment 18: The silk manufacturing system of any one of Embodiments 1 to 17 or any combination thereof, wherein the fourth processing substation comprises a microfiltration module configured to receive at least one of the silk fibroin-based solution or the purified silk fibroin-based solution and to remove microbes and reduce turbidity from the at least one of the silk fibroin-based solution or the purified silk fibroin-based solution.

Embodiment 19: The silk manufacturing system of any one of Embodiments 1 to 18 or any combination thereof, wherein the microfiltration module includes two filter stages, the first filter stage having a pore size between about 0.7 μm and about 5 μm and the second filter stage has a pore size between about 0.05 μm and about 0.8 μm, and the silk fibroin-based solution passes through the first filter stage prior to passing through the second filter stage.

Embodiment 20: The silk manufacturing system of any one of Embodiments 1 to 19 or any combination thereof, wherein the microfiltration module further comprises one or more pumps configured to transfer the silk fibroin-based solution between filter stages, between processing substations, to another process as necessary after completing the microfiltration process, or any combination thereof.

Embodiment 21: The silk manufacturing system of any one of Embodiments 1 to 20 or any combination thereof, wherein the microfiltration module further comprises one or more holding tanks, wherein the tanks may be configured to provide additional processing, including one or more of storing the solution, temperature control of the solution, or adjusting the solution concentration to address turbidity or sterility levels.

Embodiment 22: The silk manufacturing system of any one of Embodiments 1 to 21 or any combination thereof, wherein the reactor vessel is sized to have an aspect ratio of height to diameter as defined by a work volume of about 0.5 to about 5.0.

Embodiment 23: The silk manufacturing system of any one of Embodiments 1 to 22 or any combination thereof, wherein the reactor vessel is sized to have an aspect ratio of height to diameter as defined by a work volume of about 0.8 to about 2.0.

Embodiment 24: The silk manufacturing system of any one of Embodiments 1 to 23 or any combination thereof, wherein the reactor vessel further comprises a handling structure for controlling at least one of movement or position of the silk inputs within the vessel.

Embodiment 25: The silk manufacturing system of any one of Embodiments 1 to 24 or any combination thereof, further comprising a pre-treatment system configured to condition the silk inputs prior to or at introduction to the first processing substation.

Embodiment 26: The silk manufacturing system of any one of Embodiments 1 to 25 or any combination thereof, wherein the second processing substation further comprises a heat exchange system to control a temperature of the silk fibroin-based solution during processing.

Embodiment 27: The silk manufacturing system of any one of Embodiments 1 to 26 or any combination thereof, wherein the filtration module is configured to remove the second compound from the silk fibroin-based solution by circulating the silk fibroin-based solution through the filtration module until about 5 diavolumes to about at least 8 diavolumes are reached.

Embodiment 28: A method of processing silk inputs to obtain silk fibroin that comprises the steps of introducing a plurality of silk inputs to a reactor vessel; introducing a solvent to the reactor vessel; introducing a first compound to the reactor vessel; introducing heat to the reactor vessel contents to promote degumming of the silk inputs; controlling movement or positioning of the silk inputs within the reactor vessel; rinsing the degummed silk inputs; introducing a second compound to the reactor vessel to dissolve any remaining silk fibroin proteins into solution; agitating the contents of the reactor vessel; filtering the contents of the reactor vessel to substantially remove the second compound and produce a purified silk fibroin-based solution; and powderizing the purified silk fibroin-based solution to obtain the purified silk fibroin in a powder form.

Embodiment 29: A method of processing silk inputs to obtain silk fibroin that comprises the steps of introducing a plurality of silk inputs to a reactor vessel; introducing a solvent to the reactor vessel; introducing a first compound to the reactor vessel; introducing heat to contents of the reactor vessel to promote degumming of the cocoons; controlling movement or positioning of the silk inputs within the reactor vessel; removing at least a portion of the solvent and any degumming residue; rinsing the degummed silk inputs; introducing a second compound to the reactor vessel to dissolve the remaining silk fibroin proteins in to solution; agitating the contents of the reactor vessel; filtering the contents of the reactor vessel to substantially remove the second compound and produce a purified silk fibroin-based solution; directing the purified silk fibroin-based solution to a sterilization process to obtain a sterilized silk fibroin-based solution; and powderizing the sterilized silk fibroin-based solution to obtain the silk fibroin in a powder form.

Embodiment 30: A method of processing silk inputs to obtain food grade silk fibroin that comprises the steps of providing a reactor vessel configured to extract silk fibroin proteins via degumming, rinsing, and dissolving processes therein, wherein the vessel comprises at least one inlet port, at least one outlet port; and a liquid jacket configured to provide heat exchange with the vessel and its contents; introducing a plurality of silk inputs to the reactor vessel via the at least one inlet port; introducing a solvent to the reactor vessel via the at least one inlet port; introducing a first compound to the reactor vessel via the at least one inlet port; heating the contents of the reactor vessel via the liquid jacket to a temperature of about 50° C. to about 150° C. to promote degumming of the silk inputs; controlling movement or positioning of the silk inputs within the reactor vessel; removing at least a portion of the solvent and any degumming residue via the at least one outlet port; rinsing the degummed silk inputs; introducing a second compound to the reactor vessel via the at least one inlet port to dissolve the remaining silk fibroin proteins to form a silk fibroin-based solution; agitating the contents of the reactor vessel; outputting the silk fibroin-based solution including the second compound to a filtration module via the at least one outlet port; filtering the silk fibroin-based solution including the second compound to substantially remove the second compound and produce a purified silk fibroin-based solution, wherein the filtration module is configured to remove the second compound from the silk fibroin-based solution by circulating the silk fibroin-based solution through the filtration module until about 1 diavolume to about at least 12 diavolumes are reached; and powderizing the purified silk fibroin-based solution via a spray dryer to obtain the silk fibroin in a powder form such that the water activity level of the powder is less than 0.9.

Embodiment 31: A method of processing silk inputs to obtain food grade silk fibroin that comprises the steps of providing a reactor vessel configured to extract silk fibroin proteins via degumming, rinsing, and dissolving processes therein, wherein the vessel comprises at least one inlet port, at least one outlet port; and a liquid jacket configured to provide heat exchange with the vessel and its contents; introducing a plurality of silk inputs to the reactor vessel via the at least one inlet port; introducing a solvent to the reactor vessel via the at least one inlet port; introducing a first compound to the reactor vessel via the at least one inlet port; heating the contents of the reactor vessel via the liquid jacket to a temperature of about 50° C. to about 150° C. to promote degumming of the silk inputs; controlling movement or positioning of the silk inputs within the reactor vessel; removing at least a portion of the solvent and any degumming residue via the at least one outlet port; rinsing the degummed silk inputs such that the silk inputs are substantially free of sericin; introducing a second compound to the reactor vessel via the at least one inlet port to dissolve the remaining silk fibroin proteins to form a silk fibroin-based solution; agitating the contents of the reactor vessel; sterilizing the silk fibroin-based solution to obtain a sterilized silk fibroin-based solution; outputting the sterilized silk fibroin-based solution including the second compound to a filtration module via the at least one outlet port; filtering the silk fibroin-based solution including the second compound to substantially remove the second compound and produce a purified silk fibroin-based solution, wherein the filtration module is configured to remove the second compound from the silk fibroin-based solution by circulating the silk fibroin-based solution through the filtration module until about 1 diavolume to about at least 12 diavolumes are reached, wherein the purified silk fibroin-based solution comprises less than about 650 parts per million (ppm) of one or more salts or non-organic particulates; and powderizing the purified silk fibroin-based solution via a spray dryer to obtain the silk fibroin in a powder form such that the water activity level of the powder is less than 0.9.

Embodiment 32: The silk manufacturing system of any one of Embodiments 28 to 31 or any combination thereof, wherein the silk inputs come from a *Bombyx mori* silkworm.

Embodiment 33: The silk manufacturing system of any one of Embodiments 28 to 32 or any combination thereof, wherein a packing density of the silk inputs in the reactor vessel is between about 1% and about 70%.

Embodiment 34: The silk manufacturing system of any one of Embodiments 28 to 33 or any combination thereof, wherein a packing density of the silk inputs in the reactor vessel is greater than 5%.

Embodiment 35: The silk manufacturing system of any one of Embodiments 28 to 34 or any combination thereof, wherein a packing density of the silk inputs in the reactor vessel is greater than 15%.

Embodiment 36: The silk manufacturing system of any one of Embodiments 28 to 35 or any combination thereof, wherein a packing density of the silk inputs in the reactor vessel is greater than 25%.

Embodiment 37: The silk manufacturing system of any one of Embodiments 28 to 36 or any combination thereof, wherein the filtering step comprises purifying the silk fibroin-based solution via diafiltration.

Embodiment 38: The silk manufacturing system of any one of Embodiments 28 to 37 or any combination thereof, wherein the filtering step comprises purifying the silk fibroin-based solution via tangential flow filtration.

Embodiment 39: The silk manufacturing system of any one of Embodiments 28 to 38 or any combination thereof, wherein the method further comprises the step of performing a sterilization process to obtain a food grade quality silk fibroin-based solution prior to the powderizing step.

Embodiment 40: The silk manufacturing system of any one of Embodiments 28 to 39 or any combination thereof, wherein the sterilization process comprises the step of directing the purified silk fibroin-based solution to a microfiltration module.

Embodiment 41: The silk manufacturing system of any one of Embodiments 28 to 40 or any combination thereof, wherein the step of directing the purified silk fibroin-based solution to a microfiltration module comprises directing the purified silk fibroin-based solution through a first microfiltration stage having a pore size between about 0.7 µm and about 5 µm and directing the purified silk fibroin-based solution through a second microfiltration stage having a pore size between about 0.05 µm and about 0.8 µm.

Embodiment 42: The silk manufacturing system of any one of Embodiments 28 to 41 or any combination thereof, further comprising the step of adjusting a temperature of the silk fibroin-based solution during processing.

Embodiment 43: The silk manufacturing system of any one of Embodiments 28 to 42 or any combination thereof, further comprising a post-powderization step comprising at least one of: agglomerating the silk fibroin powder, conditioning the silk fibroin powder, testing the silk fibroin powder, or packaging the silk fibroin powder into, for example, a food-safe container.

Embodiment 44: The silk manufacturing system of any one of Embodiments 28 to 43 or any combination thereof, wherein the filtering step comprises utilizing at least one spiral wound membrane.

Embodiment 45: The silk manufacturing system of any one of Embodiments 28 to 44 or any combination thereof, wherein the at least one inlet port comprises a first inlet port configured to receive the silk inputs, the first compound, and the second compound and a second inlet port configured to receive the solvent; and the at least one outlet port comprises a first outlet port configured to output the silk fibroin-based solution and a second outlet port configured to output at least a portion of the solvent and any degumming residue.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Accordingly, these and other objects, along with advantages and features of the present disclosure herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure and are not intended as a definition of the limits of the disclosure. For purposes of clarity, not every component may be labeled in every drawing. In the following description, various embodiments of the present disclosure are described with reference to the following drawings, in which:

FIGS. 9A-9C show examples of screens for integration with a silk manufacturing process in accordance with one or more embodiments of the disclosure;

DETAILED DESCRIPTION

Figure 1:
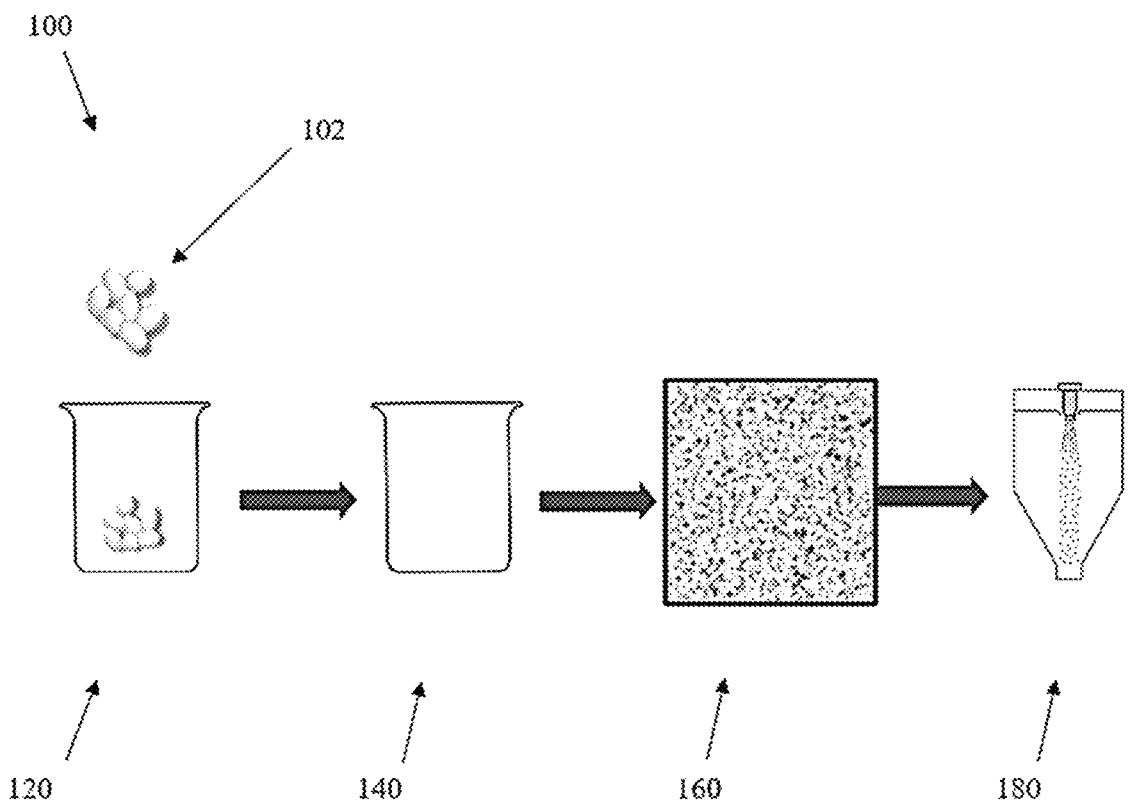
FIG. 1 shows an example of a silk manufacturing process in accordance with one or more embodiments of the disclosure.

Some implementations of the present disclosure will now be described more fully hereinafter with reference to the accompanying figures, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art.

Unless specified otherwise or clear from context, references to first, second, third or the like should not be construed to imply a particular order. A feature described as being above another feature (unless specified otherwise or clear from context) may instead be below, and vice versa; and similarly, features described as being to the left of another feature may instead be to the right, and vice versa. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

The disclosure relates to systems and methods for improving the manufacturing of silk fibroin-based solutions containing silk fibroin from silk cocoons.

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. In one embodiment, "no more than 100" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever embodiments are described herein with the language "comprising," otherwise analogous embodiments described in terms of "consisting of" and/or "consisting essentially of" are also provided. The term "consisting of" excludes any element, step, or ingredient not specified in the claim. In one embodiment, "consisting of" is defined as "closing the claim to the inclusion of materials other than those recited except for impurities ordinarily associated therewith. A claim which depends from a claim which "consists of" the recited elements or steps cannot add an element or step. The terms "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. In one embodiment, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. In one embodiment, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding further embodiments of the disclosure, without any restrictions regarding the scope of the disclosure, and without any restriction regarding the possibility of combining the features introduced in such way with other optional or non-optional features of the disclosure.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numerical ranges are inclusive of the numbers defining the range. Additionally, where multiples of the same components are described, the multiples may be referred to individually (e. ##a, ##b, ##c, etc.) or collectively (##).

DESCRIPTION

FIG. 1 depicts a process 100 for manufacturing a silk fibroin-based solution and obtaining silk-fibroin in a powder form. Specifically, the process 100 includes performing a degumming process (step 120) for extracting silk fibroin from silkworm cocoons 102 and then a dissolution process on the degummed silk fibroin (step 140) where the silk fibroin is dissolved in a heated chaotropic agent solution. Next, the process 100 includes exposing the fibroin-based solution to a purification process (step 160) where the chaotropic agent is removed from the dissolved silk fibroin solution, and finally, the silk fibroin solution is dried to obtain the silk fibroin (e.g., via powderization) (step 180). The quality of the silk fibroin obtained may be improved by improving the quality of the silk fibroin-based solution.

During the manufacturing process of silk fibroin solution, a process can be used to reduce turbidity and kill microbes to obtain a silk fibroin solution that contains the desired performance and safety requirements. Excess turbidity is undesirable in the silk fibroin solution because it may impact the tackiness of a coating made from the silk fibroin-based solution, hinder the barrier forming properties of the silk fibroin-based solution, and may cause a coating formed from the silk fibroin-based solution to look cloudy or milky. For this reason, turbidity should be kept under about 0.800 optical density measured at a wavelength of 600 nm (OD660). Accordingly, methods to meet these requirements are desirable and may include, for example, the integration of a sterilization step/substation (see 1110 in FIG. 5A and 610a/b in FIG. 7) as described herein.

Generally, the various systems and substations described herein may be interconnected via conventional plumbing techniques and may include any number and combination of components, such as pumps, valves, sensors, gauges, etc., to monitor and control the operation of the various systems and processes described herein, either manually or automatically. The various components made from materials suitable for the temperatures and materials to which they are exposed and may be used in conjunction with a controller as described herein.

Figure 2:
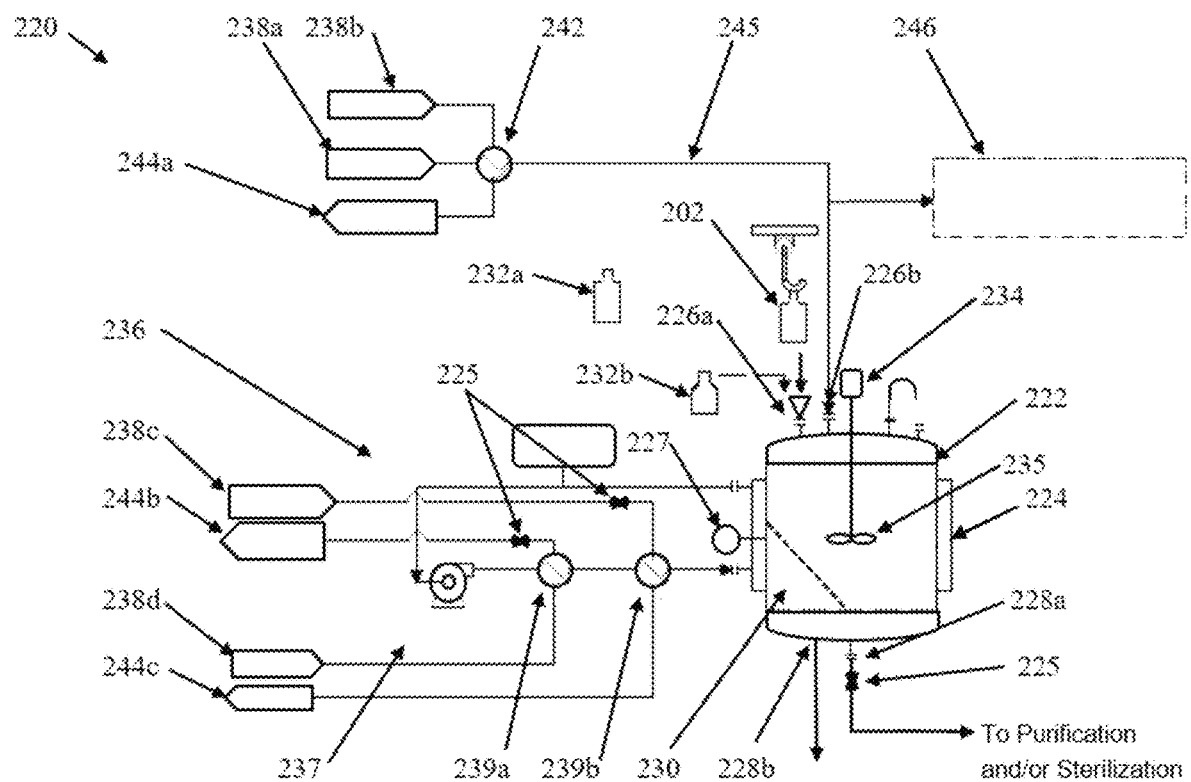
FIG. 2 shows an example of a first processing substation for use in a silk manufacturing process in accordance with one or more embodiments of the disclosure.

FIG. 2 depicts a first substation 220 configured for receiving the silkworm cocoons 202 and performing degumming, dissolving, and rinsing operations on the silkworm cocoons to obtain a silk fibroin-based solution. Ideally the silk fibroin-based solution would be substantially free of sericin after the degumming process. As shown, the substation 220 includes a reactor vessel 222 having a first inlet port 226a configured to receive the silkworm cocoons 202 and one or more ingredients 232a, b (e.g., soda ash, a chaotropic agent), a second inlet port 226b configured to receive a solvent (e.g., water), and at least one outlet 228a configured to output the silk fibroin-based solution. The reactor vessel 222 is configured to process the silkworm cocoons into a silk fibroin solution by at least one of degumming, rinsing, and dissolving within the single glass-lined vessel. In alternative arrangements, one or more first substations generally, and one or more reactor vessels specifically, may be provided to suit a particular application. See, for example, FIGS. 7A-7C. In some examples, multiple smaller vessels may be used to optimize the process by, for example, making the heating and cooling of the solution more efficient. In some embodiments, the substation 220 includes a heat exchanger 242 for conditioning the solvent prior to introduction into the vessel 222.

The first processing substation 220 also includes a water or oil jacket 224 disposed about the reactor vessel 222 that is configured to provide heat exchange (e.g., heating or cooling as necessary) with the vessel 222 and its contents. The water or oil jacket 224 includes a heat exchange circuit 236 that includes a pump 237 for recirculating a heating/cooling medium in fluid communication with, for example, two heat exchangers 239a, 239b that are in fluid communication with one or more of steam or cooling liquid as necessary to control the temperature of the contents of the vessel 222. The first processing substation 220 also has the ability to pressurize its contents. The first processing substation is configured to pressurize the contents to a pounds per square inch (psi) of about 0 psi to about 20 psi, from about 0 to about 10 psi, from about 0 to about 5 psi, from about 0.1 to about 20 psi, from about 0.1 psi to about 10 psi, and from about 0.1 psi to about 5 psi. The pressure can be applied during any of the steps to obtain a silk fibroin-based solution, including degumming, rinsing, and dissolving.

The first processing substation 220 also includes a plurality of inputs and outputs 238a, b, c, d, 244a, b, c for introducing and/or removing a solvent, steam, cooling water, condensate, etc. to, for example, the vessel 222 and/or the water or oil jacket 224 via their corresponding inlets/outlets. For example, in some embodiments, input 238a is configured to introduce softened water 245 to the heat exchanger 242 and then to the vessel 222 via the inlet 226b, inputs 238b, 238c introduce steam to the heat exchangers 242 and 239b respectively, and input 238d introduces cooling water to one of the heat exchangers 239a. The outputs 244a, 244b, 244c are configured to remove the condensate and cooling water from the heat exchangers 239a, b, 242. In other embodiments oil can be substituted for water to achieve the same cooling or heating requirements.

The first processing substation 220 may further include equipment 234 configured to agitate the contents of the reactor vessel 222, such as, for example, a mixer, a vibration plate, a magnetic stirrer, sonicator, liquid jet streams, air streams, etc. In various embodiments, the agitation equipment 234 may be disposed proximate a bottom surface of the reactor vessel 222. In some embodiments, the agitation equipment 234 is a mixer having a unitary shall and impeller 235. The impeller 235 may be configured for axial flow, radial flow, and/or tangential flow, and may be run in reverse. Additionally, the impeller 235 may be coated with a substance to resist attachment of silk fibers and/or have a surface finish of the blades (e.g., a surface roughness below some threshold value). The mixer may have interchangeable impellers, where the impellers may be configured to suit particular processes and have one or more of flat blades, curved blades, pitched blades, finger blades, anchor blades, gate blades, ribbon blades, etc. having different shapes, pitch, etc. In some embodiments, the impeller assembly includes a slidable sleeve that may be configured to compress the cocoons and/or remove build-up on the impeller (e.g., push or scrap the cocoons off of the impeller).

In further embodiments, the reactor vessel 222 includes a second outlet 228b for removing at least a portion of the solvent and any residue therein (e.g., dissolved sericin), which can be sent to waste, recirculated, or recycled. The reactor vessel 222 may be sized to have an aspect ratio of height to diameter as defined by a work volume. The volume of the vessel will vary to suit a particular application (e.g., finished yields) and may range from about 0.2 liters to about 150,000 liters, preferably about 0.5 liters to about 5,000 liters. The vessel contents may include a plurality of silkworm cocoons 202 (with or without pre-treatment), a solvent 244e (e.g., water), and a compound. The water or oil jacket 224 is configured to heat the contents to a temperature of about 50° C. to about 150° C., preferably about 85° C. to about 125° C. Generally, the process times, temperatures, pH, and other solution characteristics may vary to suit a particular application, such as the type of silk source.

The reactor vessel 222 may also include a handling structure or equipment 230 configured to control the movement and/or the position of the silkworm cocoons 202 within the vessel 222 (e.g., prevent floating of the cocoons). The equipment 230 may include, for example, a screen or netting disposed proximate a lower portion of the vessel 222 and configured to separate the silkworm cocoons from the agitation equipment 234, a chute or funnel structure in communication with the first inlet and configured to direct the silkworm cocoons to a particular location within the vessel 222 during introduction thereof, a recirculation system configured to draw a portion of the solution from a lower portion of the vessel 222 and reintroduce the solution to an upper portion of the vessel 222 and/or introduce fresh water to push the silkworm cocoons down into the solution, a vertically movable sieve (e.g., a perforated plunger or a vented, floating lid) disposed within the vessel and configured to "push" any solids within the solution towards a lower portion of the vessel, one or more spray balls, and one or more baffles disposed within the vessel and extending from an inner wall thereof, where the baffles direct the movement of the solution and contents therein. In one embodiment, the equipment 230 includes one or more cages or nets disposed within the vessel 222 to ensure that the silkworm cocoons are spaced throughout the vessel 222. For example, the silkworm cocoons may be separated into a plurality of spherical or cubical cages.

The first processing substation 220, and system generally, may include one or more valve assemblies 225, inlets 226a, b, and/or outlets 228a, b (with manual or automatic actuators) that are configured to control the introduction to and removal from the first processing substation and/or the reactor vessel 222 of any component, such as, for example, silkworm cocoons, compounds, solvents, waste solutions, residues, steam, cooling water, and final silk fibroin-based solutions. The first processing substation 220, and system generally, may include at least one sensor 227 configured to sense one or more of solution temperatures, concentrations, flow rates, pH, fluid levels, turbidity, particle size, molecular weight, pressure, etc., which may be used to control (with or without human intervention) the operation of the various processes. Once the desired silk fibroin-based solution has been obtained, which may be determined manually or via one or more sensed characteristics, the solution is directed (e.g., via pumps, valves, etc. as needed) to the next substation as described below. In various embodiments, the systems described herein may include a clean-in-place (CIP) module 246 (e.g., a mobile cart) that can be fluidly coupled to the substations to perform maintenance thereon.

Figure 3:
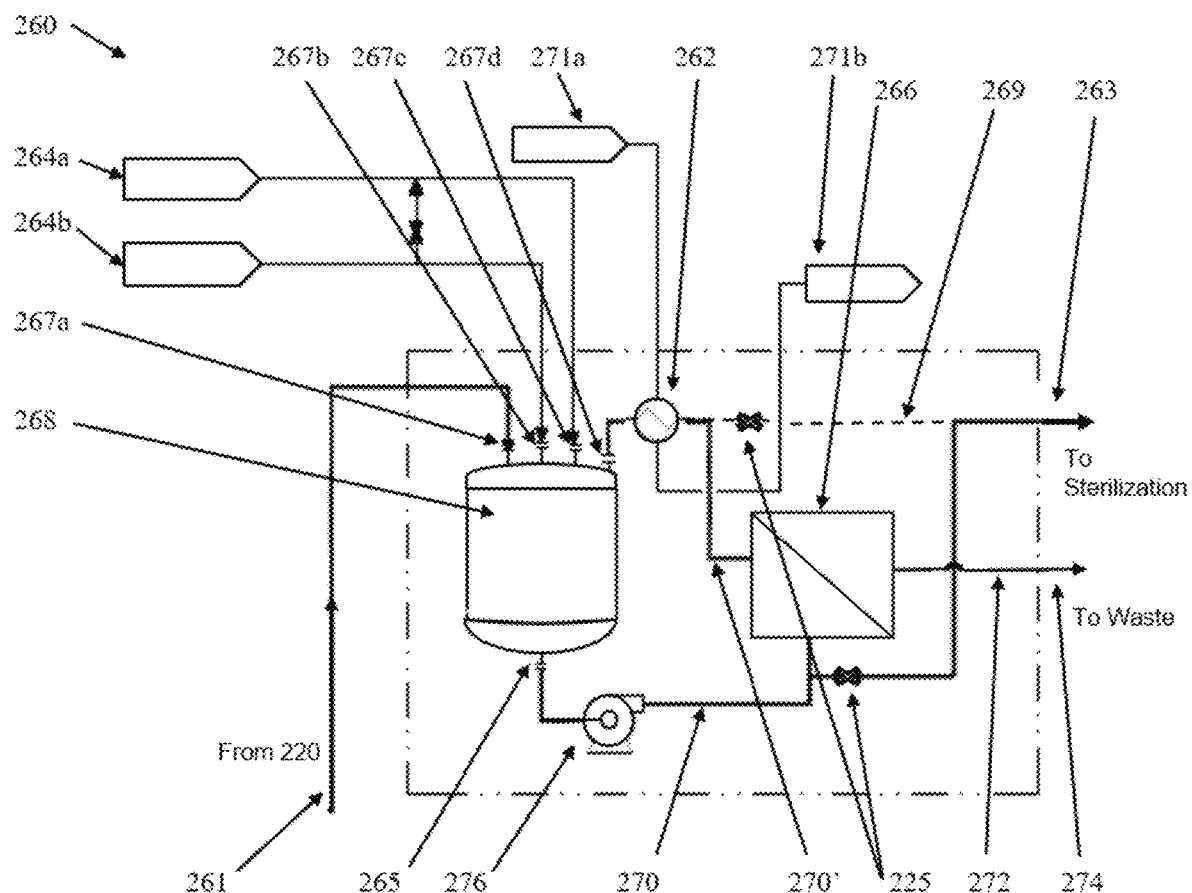
FIG. 3 shows an example of a second processing substation for use in a silk manufacturing process in accordance with one or more embodiments of the disclosure.

FIG. 3 depicts a second substation 260 configured for receiving the silk fibroin-based solution and filtering the solution to remove the chaotropic agent from the solution. As shown, the substation 260 includes a holding vessel 268 and a filtration module 266 housing at least one membrane. The substation 260 includes at least one input 261 configured to receive the silk fibroin-based solution including the chaotropic agent from the first substation 220 and at least one outlet 263 configured to output the purified silk fibroin-based solution with a reduced chaotropic agent concentration (i.e., the retentate 270, 270') and another outlet 274 configured to output a waste stream, such as the permeate 272 from the filtration module 266. The silk fibroin-based solution including the chaotropic agent is introduced to the vessel 268 via an inlet 267*a* disposed thereon.

Generally, the filtration module 266 is configured to remove the chaotropic agent from the silk fibroin-based solution via diafiltration. In some cases, the flow through the module is tangential to a surface of the membrane. The silk fibroin-based solution may also experience some level of concentration that may be beneficial in later operations. The silk fibroin-based solution may be circulated through the filtration module for a duration defined by about 1 diavolumes to about at least 12 diavolumes, preferably about 3 diavolumes to about 10 diavolumes, and more preferably about 5 diavolumes to about 9 diavolumes. In some cases, the concentrations levels of the chaotropic agent in the retentate and/or the pressure drop across the filtration module may also be monitored to determine a state of the process. The filtration module 266 may include any number and type of membranes to suit a particular application. In one embodiment, the module 266 includes one or more spiral wound membranes, which may be provided in multiple stages. For example, the silk fibroin-based solution may pass through the filtration module 266, and the various stages thereof, in series, parallel, or both to suit a particular application.

The holding vessel 268 may include one or more inlets 267*b*, 267*c* configured to introduce a rinse solution, such as a softened water (input 264*a*) or a reverse osmosis water (input 264*b*) to the silk fibroin-based solution during the filtration process. The vessel 268 further includes an outlet 265 for removing the solution 270 and directing the solution to the filtration module 266 via a pumping system 276. The at least partially purified solution 270' is directed back to the holding vessel 268 (via inlet 267*d*), where it may be exposed to additional rinsing and circulation through the filtration module 266. The permeate 272 may be output to waste (with or without further processing) or recycled if feasible. Once the solution 270, 270' has reached a desired level of purification, as determined manually or automatically, the solution 270, 270' is output to another processing substation (e.g., sterilization) via a valve arrangement 225. In some embodiments, the purified solution may be removed from the second processing system 260 via an alternative line 269 and valve assembly 225 located downstream of the filtration module 266. In some embodiments, the solution 270, 270' is output directly to the fourth processing substation 280 (FIG. 6A), 380 (FIG. 6B) rather than another substation through the outlet 263.

The second processing substation 260 may also include a heat exchange system 262, including any valves, pumps, controls, etc. as needed to control a temperature of the silk fibroin-based solution during processing. As shown in FIG. 3, the heat exchange circuit 262 is disposed in the return line to control the temperature of the at least partially purified solution 270' exiting the filtration module 266; however, the heat exchange circuit 262 may be located elsewhere to suit a particular application. The circuit 262 further includes ports 271*a*, 271*b* for introducing and/or removing a cooling (or heating) medium.

Figure 4:
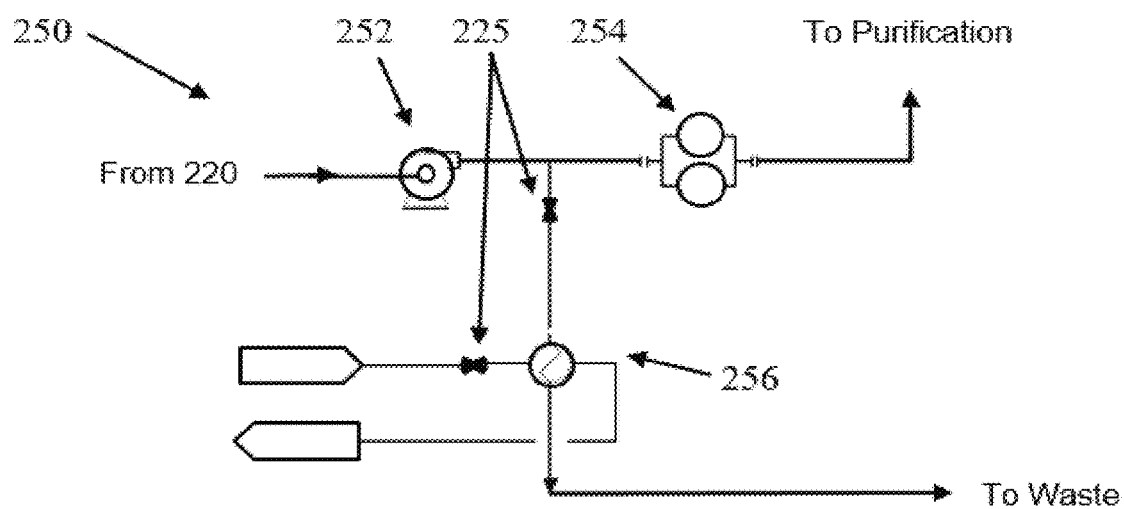
FIG. 4 shows an example of auxiliary equipment for integration with a silk manufacturing process in accordance with one or more embodiments of the disclosure.

In various embodiments of the systems disclosed herein, an optional pre-filtration substation 250 may be disposed between the first processing substation 220 and the second processing substation 260 (see FIG. 3). The pre-filtration substation 250 shown in FIG. 4 may include a transfer pump 252 to assist with the transfer of the silk fibroin-based solution to the second processing substation 260 (see FIG. 3), one or more filtration modules 254 to suit a particular application, and a heat exchange circuit 256. In some embodiments, the pre-filtration substation includes a valve assembly 225 that may be configured to bleed off a portion of the silk fibroin-based solution that may contain an excessive amount of a contaminant (e.g., sericin) to waste, with or without cooling as needed.

FIGS. 5A-5E are exemplary implementations of various third processing substations 1110, 1210, 1310, 1410, 1510 for sterilization that may be incorporated into the overall production process for a silk fibroin-based solution containing silk fibroin. These figures do not show all the possible implementations of the systems and processes and are generally shown in relationship to the second processing substations 1160, 1260, 1360, 1460, 1560.

Generally, one of the major concerns when processing the silk fibroin-based solution is that the process does not negatively impact the silk fibroin-based solution, including the silk fibroin, or its performance. For example, using a filter with a pore size that is too small could damage the shear-sensitive silk fibroin in the silk fibroin-based solution, which could reduce the barrier forming properties of the silk fibroin-based solution. In another example, a filter could remove some of the silk fibroin from the solution, altering the molecular weight (Mw) of the silk fibroin-based solution, for example, rendering the Mw too high or too low, or by narrowing the polydispersity index (PDI). As another example, the microfiltration step could reduce the volume of the silk fibroin-based solution, which should be limited. The goal of the filtration step is to provide a process that can meet all the requirements described herein, without negatively impacting the performance of the silk fibroin-based solution.

One option to obtain these results is through the sterilization process of the third processing substations 1110, 1210, 1310, 1410, 1510 described herein. The third processing substations depicted herein use microfiltration to addresses these concerns and are capable of producing a silk fibroin-based solution that falls under the allowable limits for each. Additional sterilization systems and processes are disclosed in U.S. Provisional Patent application No. 63/191,441, filed May 21, 2021, which is hereby incorporated by reference herein in its entirety. The microfiltration process could entail utilizing multiple, different types of filters, (e.g., spiral, membrane, cartridge, hollow fiber, plate and frame, cartridges with O-rings), materials, membrane structures, pore sizes, etc.), different transmembrane pressures, and/or the number and configurations of the filters (e.g., two or more filter stages arranged in a series configuration, where each filter stage may incorporate more than one filter/membrane in different configurations). Generally, the exact number and arrangement of filter stages and/or the filters included therein, along with membrane pore sizes, may vary to suit a particular application; for example, to accommodate different flow rates, volumes, target pressure drops, target turbidity levels, sterility levels, solvents used, etc.

Figure 5A:
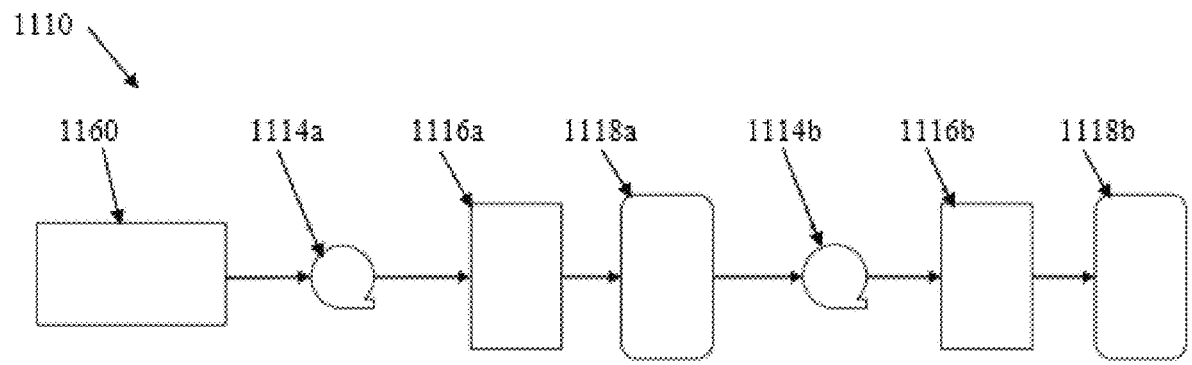
FIGS. 5A-5E show examples of various third processing substations as integrated in silk manufacturing processes in accordance with one or more embodiments of the disclosure.

FIG. 5A shows an example of the sterilization process/third processing substation 1110 incorporated with the purification process/second processing substation 1160, where the third substation 1110 is disposed downstream of the second substation 1160 and includes the use of two pumps 1114*a, b*, two filter stages 1116 *a, b*, and two holding tanks 1118 *a,b*. As shown, the path of the silk fibroin-based solution after it leaves the purification process of the second substation 1160 is directed to a first pump 1114*a*, which passes the solution to and through a first filter stage 1116*a* and into a first holding tank 1118*a*. A second pump 1114*b* in fluid communication with the first holding tank 1118*a* transfers the silk fibroin-based solution to and through a second filter stage 1116*b* and into a second holding tank 1118*b*. The silk fibroin-based solution may be directed to another process as necessary after completing the microfiltration process of the third substation 1110.

Figure 5B:
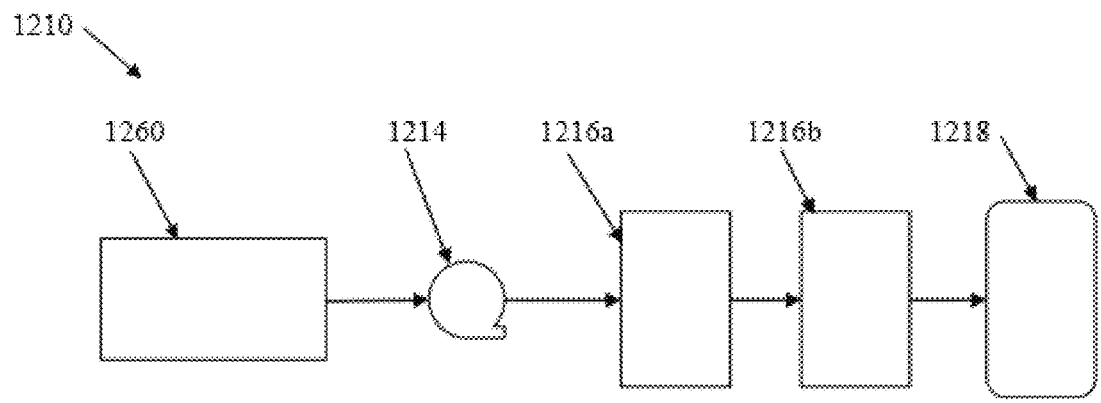

FIG. 5B shows another example of a sterilization process/third processing substation 1210, where the purification process 1260 still precedes the sterilization process/third processing substation 1210, but includes the use of one pump 1214, two filter stages 1216a, b, and one holding tank 1218. As shown, the path of the silk fibroin-based solution after it leaves the purification process of the second substation 1260 is directed to the single pump 1214, which passes the silk fibroin-based solution to and through the first filter stage 1216a and then to and through the second filter stage 1216b and into the holding tank 1218. Again, the silk fibroin-based solution may be directed to another process as necessary after completing the sterilization process, including, for example, back through the third processing substation 1210 for a second pass, quality testing, or to powderization.

Figure 5C:
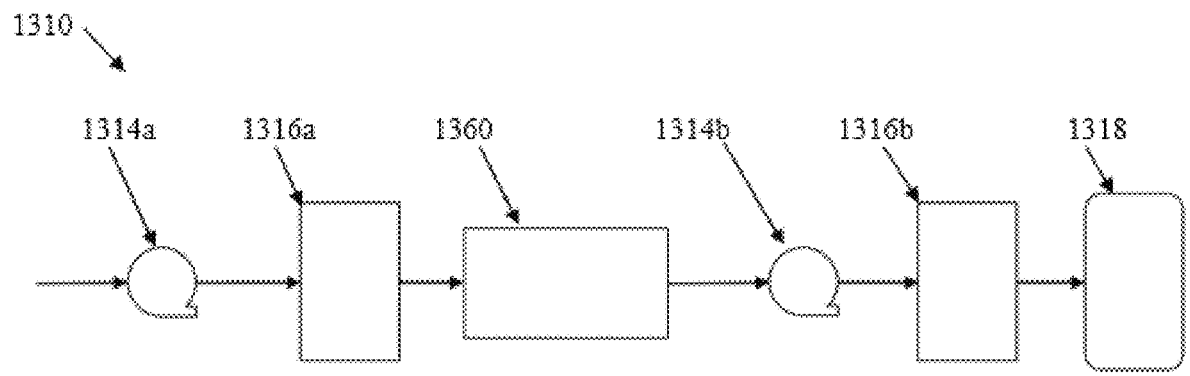

FIG. 5C shows yet another example of a sterilization process/third processing substation 1310, but where the sterilization process is incorporated with the purification process/second processing substation 1360 and includes two pumps 1314 a, b, two filter stages 1316 a, b, and one holding tank 1318. As shown, the path of the silk fibroin-based solution is introduced to the first filter stage 1316a via the first pump 1314a and then to the purification process 1360. The silk fibroin-based solution exiting the purification process 1360 is directed to the second pump 1314b, which passes the purified silk fibroin-based solution to and through the second filter stage 1316b and into the holding tank 1318. In this embodiment, the sterilization process occurs both before and after the purification process and includes the use of two pumps, two filters, and one holding tank.

Figure 5D:
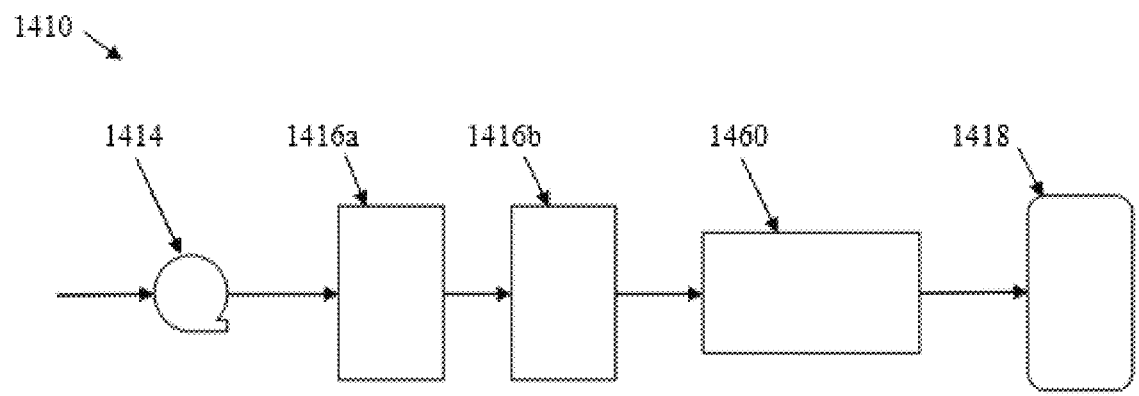

FIG. 5D shows still another example of a sterilization process/third processing substation 1410, where the sterilization process is carried out prior to the purification process 1460 and includes one pump 1414, two filter stages 1416 a, b, and one holding tank 1418. As shown, the path of the silk fibroin-based solution is introduced to the first and second filter stages 1416a, 1416b via the pump 1414 and then directed to the purification process 1460. The silk fibroin-based solution exiting the purification process 1460 is directed to the holding tank 1418. In this embodiment, the sterilization process 1410 occurs before the purification process 1460 and includes the use of one pump, two filters, and one holding tank; however, other quantities of pumps, filter stages, and tanks may be incorporated to suit a particular application.

Figure 5E:
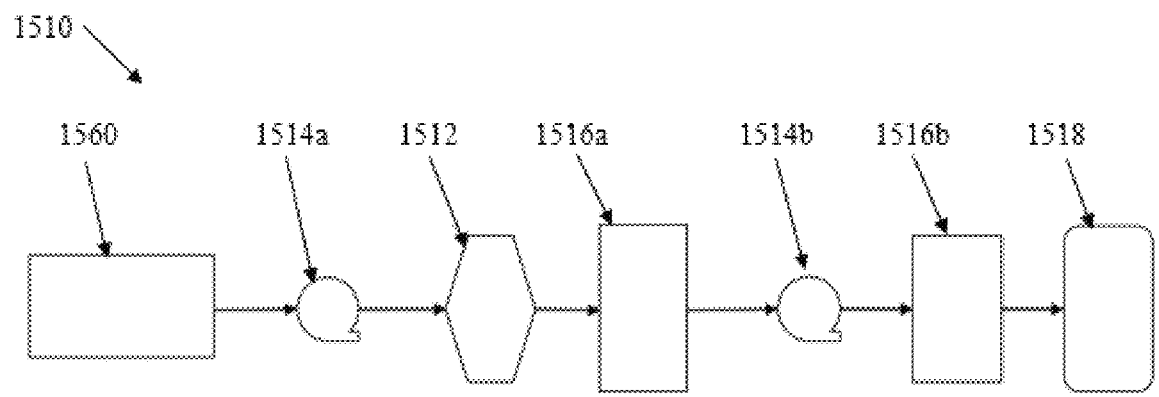

FIG. 5E shows another example of a sterilization process/third processing substation 1510 similar to some of those described above and where the purification process/second processing substation 1560 precedes the sterilization process 1510 and includes the use of two pumps 1514 a, b, two filter stages 1516 a, b, one holding tank 1518, and one auxiliary piece of equipment 1512. As shown, the path of the silk fibroin-based solution after it leaves the purification process 1560 is directed to the first pump 1514a, which first passes the solution to and through a heat exchange module 1512 that may be used to heat and/or cool the silk fibroin-based solution prior to its introduction to the first filter stage 1516a. However, the heat exchange module 1512 could be located after the first or second filter stage 1516a, 1516b and/or before the holding tank 1518. The second pump 1514b is in fluid communication with the first filter stage 1516a and transfers the silk fibroin-based solution to and through a second filter stage 1516b and into the holding tank 1518.

In other embodiments, different numbers and configurations (e.g., series or parallel) of filter stages may be used. Multiple tanks or pumps may also be used to obtain the desired throughput of the filters and proper pressure to achieve optimal filtration. Additionally, the tanks may include structure for further treating the silk fibroin-based solution to further reduce turbidity and/or microbes, such as, for example adjusting the solution composition.

Figure 6A:
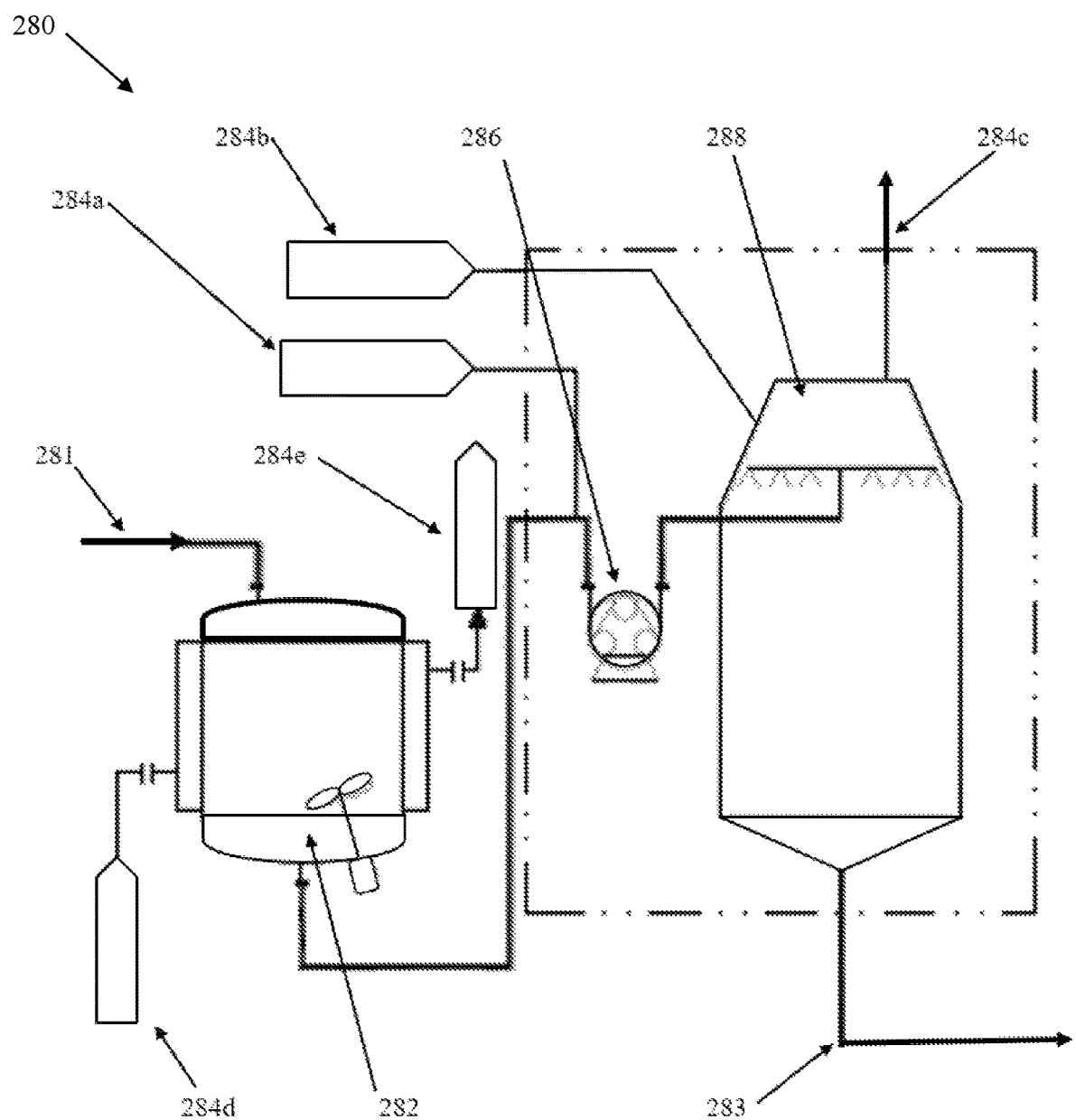
FIG. 6A shows one example of a fourth processing substation for use in a silk manufacturing process in accordance with one or more embodiments of the disclosure.
Figure 6B:
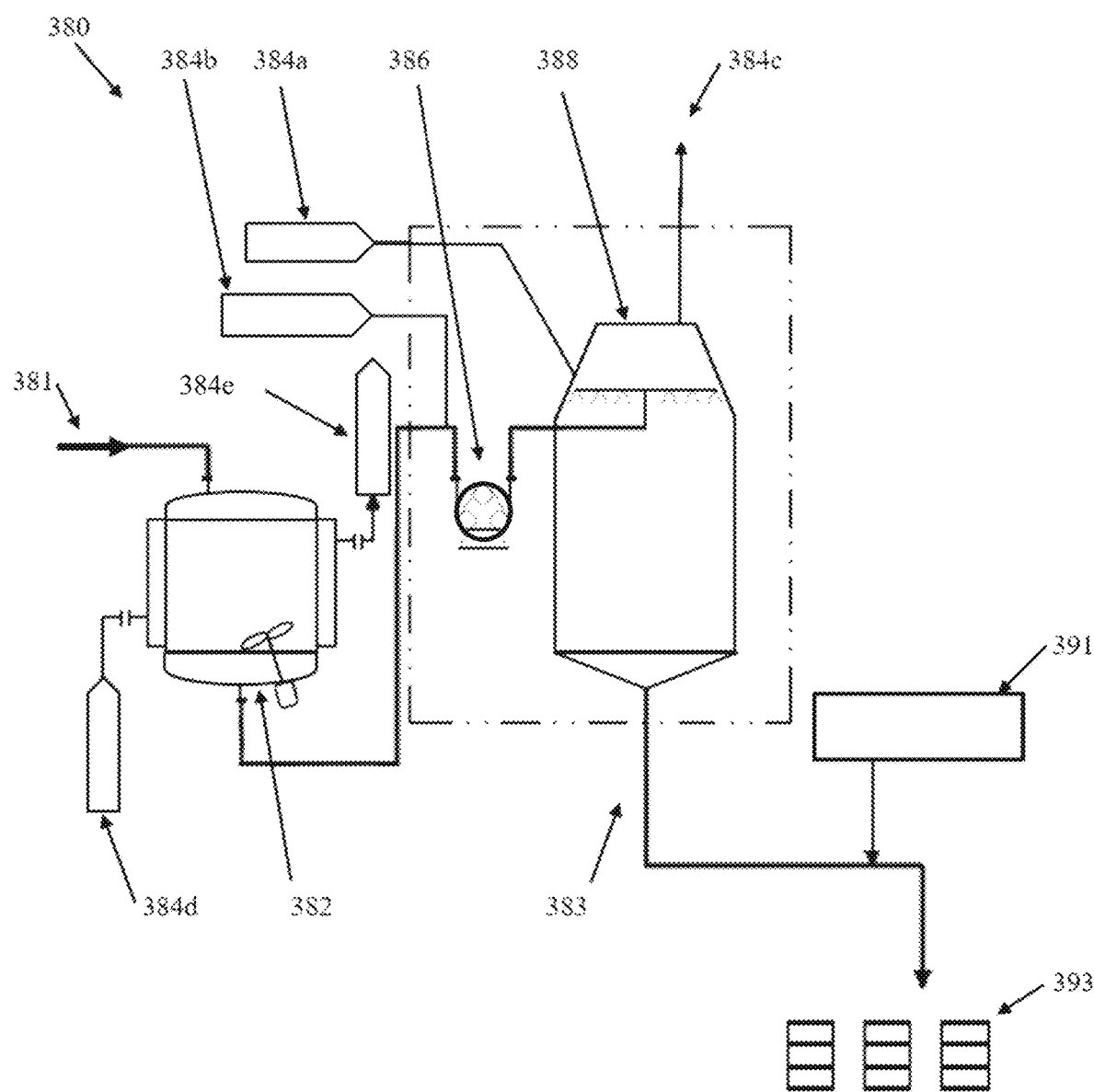
FIG. 6B shows another example of a fourth processing substation for use in a silk manufacturing process in accordance with one or more embodiments of the disclosure.

FIGS. 6A and 6B depict alternative fourth processing substations 280, 380 for powderizing the sterilized silk fibroin-based solution. As shown in FIG. 6A, the fourth substation 280 includes a dryer feed mixer vessel 282 and a spray dryer 288 in fluid communication with a plurality of inputs and outputs 284a-e (e.g., softened water 284a, compressed air 284b, exhaust 284c, chilled water in 284d, and chilled water out 284e). Generally, the fourth processing substation 280 includes an input 281 configured to receive the purified and/or sterilized silk fibroin-based solution and an output 283 configured to output a silk-fibroin powder that is easily instantizable. In some embodiments, the water activity level of the silk-fibroin powder may be from about 0.01 to about 1.0, preferably under 0.85. The dryer feed mixer vessel 282 holds the silk fibroin-based solution prior to drying and may be configured to treat the silk fibroin-based solution prior to drying to, for example, enhance powderization or produce a more instantizable powder. The silk fibroin-based solution is transferred from the vessel 282 to the spray dryer 288 via a pumping system 286. In some embodiments, silk fibroin-based solution from different batches with different molecular weight profiles (e.g., lower molecular weight silk fibroin may be added to higher molecular weight silk fibroin) may be mixed together in the feed tank prior to powderization. In some embodiments, an additive could be added to the feed tank prior to powderization. These additives can be any of those known to one of ordinary skill in the art, including kosmotropic components, humectants, anticaking agents, antifoaming, agents, oils, sugars, desiccants, catalysts, or any of those listed in US Patent Publication No. 2020-0178576 A1, which is incorporated herein by reference.

The fourth processing substation 380 depicted in FIG. 6B is substantially identical to the substation 280 of FIG. 6A, insofar as the substation 380 includes a dryer feed mixer vessel 382, a pumping system 386, and a spray dryer 388 in fluid communication with a plurality of inputs and outputs 384a-e (e.g., softened water 384a, compressed air 384b, exhaust 384c, chilled water in 384d, and chilled water out 384e) and configured to receive the purified and/or sterilized silk fibroin-based solution via an input 381 and output a silk-fibroin powder via an output 383. The fourth processing substation 380 includes additional equipment disposed downstream of, or incorporated with, the spray dryer 388. Specifically, the substation 380 includes equipment 391 for providing an additive(s) to the silk fibroin powder or otherwise conditioning the powder for, for example, enhanced performance. In one embodiment, the equipment 391 is agglomeration equipment, such as an external fluid bed or a fluid bed integrated with the powderization equipment. The agglomeration equipment may aid in agglomeration of the powdered silk fibroin protein, which may improve dispersibility, instantization, or wettability properties of the powdered silk fibroin protein. Any suitable agglomeration equipment may be utilized. The substation also includes packaging equipment 393 for appropriately packaging the silk fibroin powder.

Figure 7A:
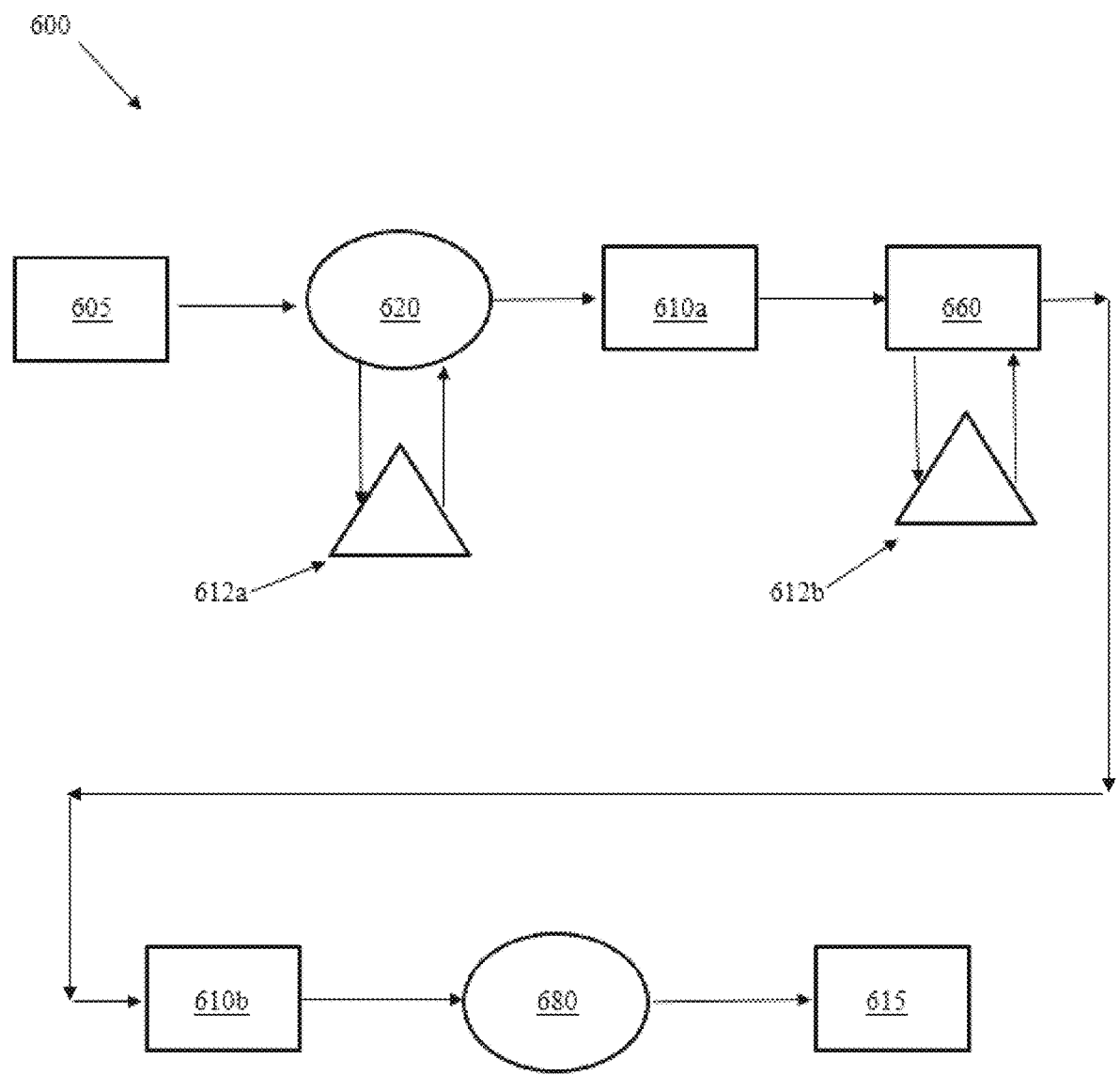
FIGS. 7A-7D show alternative examples of silk manufacturing processes in accordance with one or more embodiments of the disclosure.
Figure 7B:
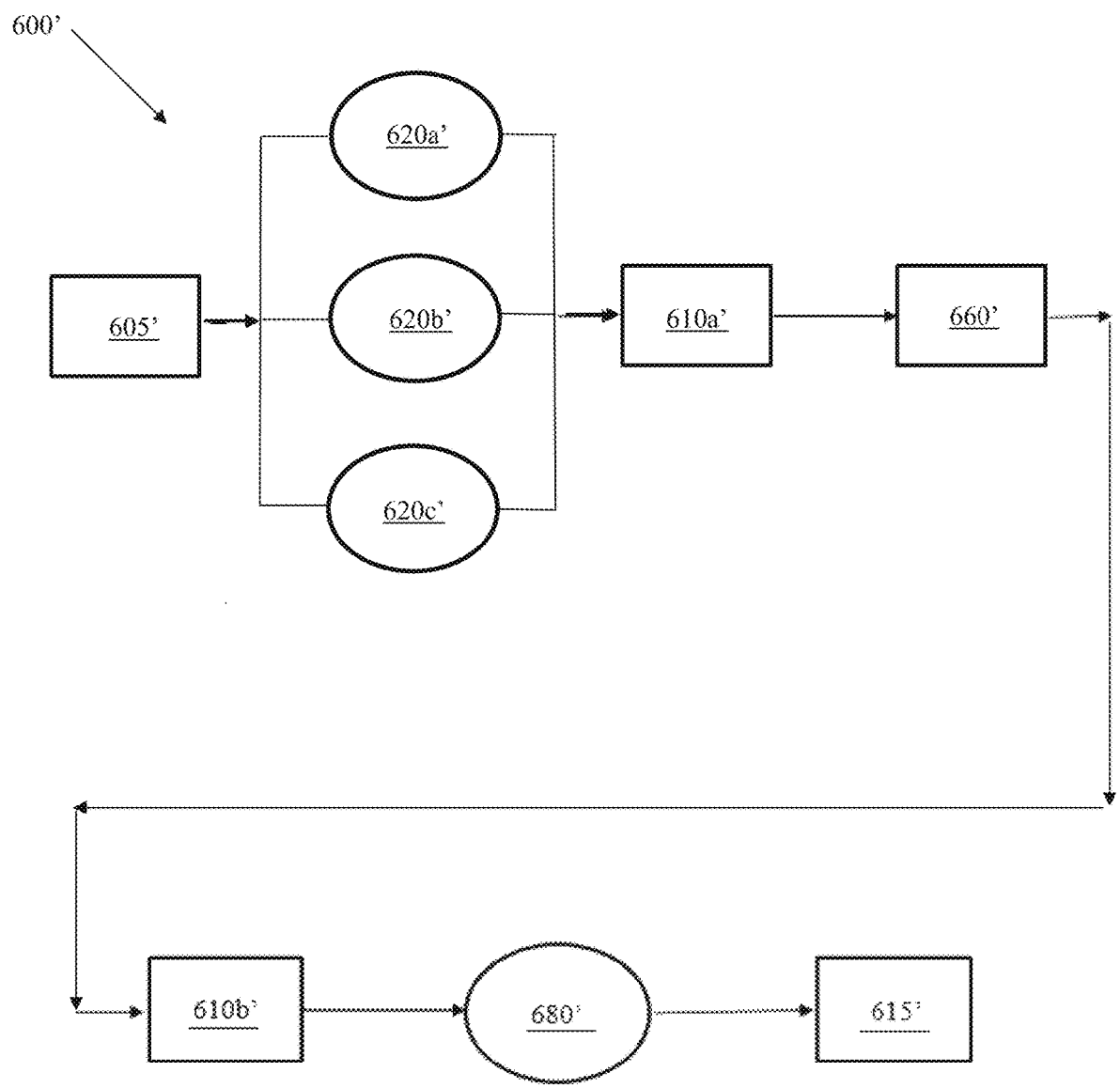
Figure 7C:
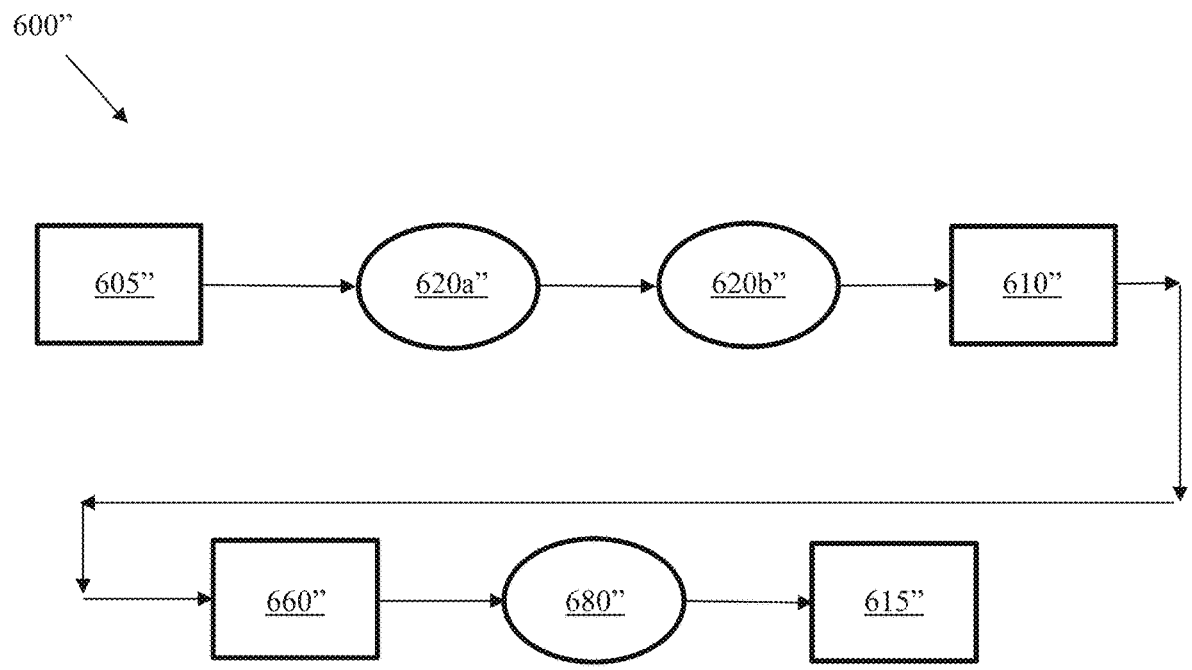
Figure 7D:
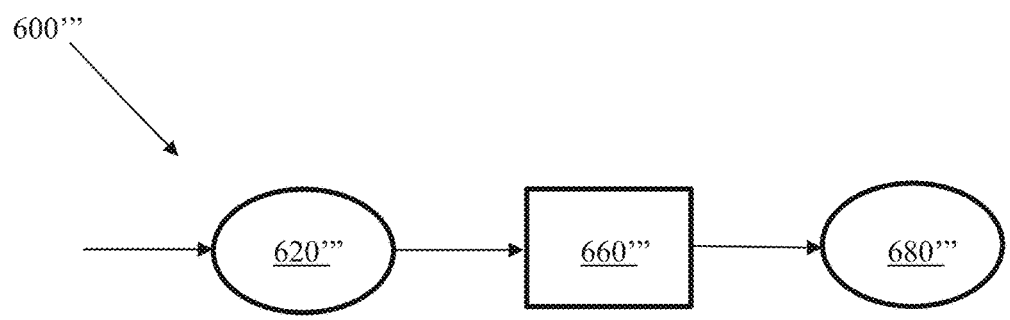
Figure 8:
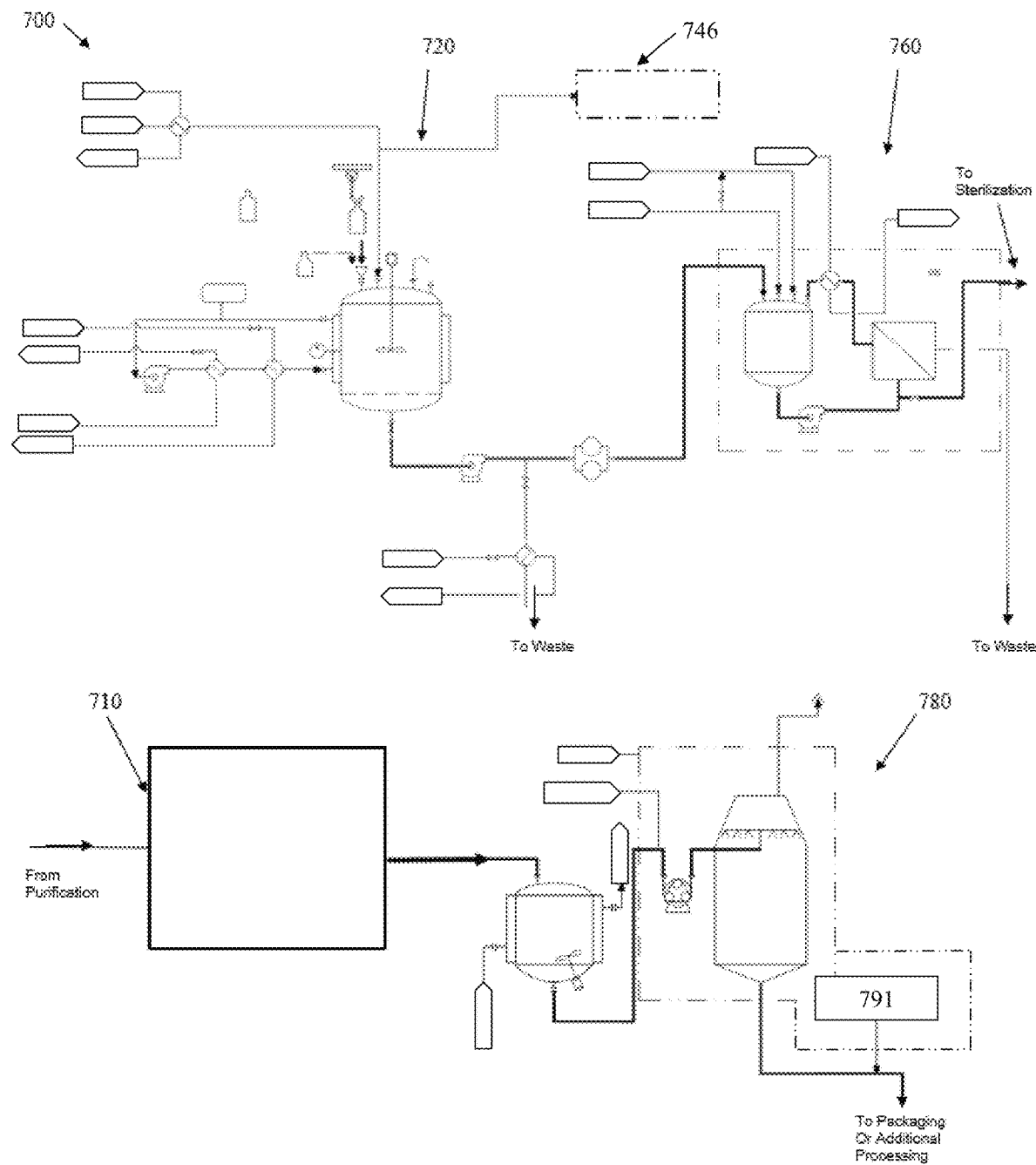
FIG. 8 shows yet another example of a silk manufacturing process in accordance with one or more embodiments of the disclosure.

FIGS. 7 and 8 depict alternative examples of systems and processes for manufacturing silk-fibroin solutions and obtaining a silk fibroin powder therefrom.

Generally, FIGS. 7A-7D depict alternative systems/processes 600, 600', 600", 600''' for manufacturing a silk fibroin solution. The system 600 of FIG. 7A includes an optional pre-treatment substation 605 for pre-treating the silkworm cocoons (e.g., shredding, soaking, pupae removal (e.g., sieve, vibrating screen, etc.), etc.) and a first processing substation 620 downstream thereof for performing a degumming, rinsing, and dissolution process to obtain a silk fibroin-based solution, with an optional heat exchange substation 612a for conditioning the solution. In some embodiments, the pre-treatment substation 605 may include a continuous soaking process where the silkworm cocoons are soaked in a heated solution (e.g., water comprising the first compound) and then fed to the reactor vessel, with or without dewatering. In addition, during processing in the first processing substation 620, the reactor vessel may be drained, refilled, and reheated at various stages of the process (e.g., at the halfway point) and/or multiple degumming processes carried out.

Disposed downstream of the first substation 620 and in fluid communication therewith is a first sterilization module 610a of a third processing substation for treating the silk fibroin-based solution prior to purifying the solution at the second processing substation 660. The second processing substation 660 may include an optional heat exchange substation 612b. Next, the solution is directed to a second sterilization module 610b of the third processing substation, and then the sterilized silk fibroin-based solution is transferred to a fourth processing substation 680 for powderizing the silk fibroin-based solution. The silk fibroin powder may then be directed to an optional post-treatment substation 615 for additional processing and/or packaging. The systems and processes described herein may include additional or different processing substations as necessary to suit a particular application.

The systems 600', 600" of FIGS. 7B and 7C are similar to the system 600 described above insofar as they include an optional pre-treatment substation 605', 605", one or more first processing substations 620a', b', c', 620a", b", one or more sterilization modules 610a', b', 610" (i.e., third processing substation), a second processing substation 660', 660" for purifying the solution, a fourth processing substation 680', 680" for powderizing the silk fibroin-based solution, and an optional post-treatment substation 615', 615". Specifically, the system 600' depicted in FIG. 7B incorporates multiple first processing substations (or multiple DRD vessels) 620a', 620b', 620c' arranged in parallel. For example, multiple smaller substations may be used in parallel to speed up production and/or accommodate a particular plant footprint. The system 600" depicted in FIG. 7C also includes multiple first processing substations (or multiple DRD vessels) 620a", 620b", but arranged in series. In some embodiments, a system 600''' as shown in FIG. 7D is used. The system 600''' includes one or more first processing substations 620''' for performing a degumming, rinsing, and dissolution process to obtain a silk fibroin-based solution, one or more second processing substations 660''' for purifying the solution, and one or more fourth processing substations 680''' for powderizing the silk fibroin-based solution. Generally, the specific number and arrangement of the first processing substations 620, 620', 620", 620''' may vary to suit a particular application.

FIG. 8 depicts a system/process 700 for manufacturing a silk fibroin solution that includes a first processing substation 720, a second processing substation 760 disposed downstream of the first substation, a third processing substation 710 disposed downstream of the second substation, and a fourth processing substation 780 disposed downstream of the third substation. The various substations are similar to those described herein (e.g., 746=246, 791=391, etc.), insofar as the first substation 720 is configured to receive a plurality of cocoons, a solvent, and one or more compounds for processing to obtain a silk fibroin-based solution; the second substation is configured to filter the silk fibroin-based solution to substantially remove one or more compounds and produce a purified silk fibroin-based solution; the third substation is configured to receive the purified silk fibroin-based solution and sterilize same to obtain a "food grade" quality silk fibroin-based solution; and the fourth substation is configured to powderize the purified and sterilized silk fibroin-based solutions to obtain the silk fibroin in a powder form. Many modifications and other implementations of the disclosure will come to mind to one skilled in the art to which this disclosure pertains having the benefit of the teachings presented in the foregoing descriptions and the associated figures. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

FIGS. 9A-9C depict different configurations (top and front views) of screens 930, 930', 930" that may be integrated into the systems disclosed herein, for example, within the first processing substation generally or the reactor vessel specifically, to, for example, help control movement of the cocoons. The screen 930 depicted in FIG. 9A includes a ring 988 with a conical shaped basket 990 extending therefrom. The basket 990 includes a plurality of perforations 992 that permit flow therethrough (e.g., liquids, possibly along with other components that are smaller than the perforations and typically deemed desirable and/or insignificant). Generally, the ring 988 may be configured to provide an interface to the equipment (e.g., attachment to the bottom of the vessel via a flange assembly), support to the basket 990, and/or means for handling the screen 930. The screen 930 of FIG. 9A includes an optional handle 994. The screen 930' depicted in FIG. 9B also includes a ring 988' and a basket 990' extending therefrom, where the basket 990' has a generally tapered or frusto-conical shape (also known as a Pilgrim's Hat) and also includes a plurality of perforations 992' formed therein. The screen 930" depicted in FIG. 9C also includes a ring 988" and a basket 990" extending therefrom, where the basket 990" has a generally cylindrical or oblong shape and includes a plurality of openings 992" formed therein. In some embodiments, the basket 990" may be constructed from a woven mesh screen, with the wire size, spacing, % open area, etc. selected to suit a particular application as disclosed below.

Generally, the screens 930, 930', 930" can be used to ensure that undesirable aspects of the silk fibroin solution do not flow through the outlet (928a in FIG. 10 and 1028a in FIG. 11), including silk fibroin (including fragments) and debris included within the silkworm cocoons (e.g., silkworms, organic material (plant material, soil, etc.), inorganic material (packaging, ties, etc.)). It should be understood that the sizes, shapes (cylindrical, rectangular, bowl, etc.), perforation type, opening sizes, open area, and distribution (e.g., whether perforations 992, 992', 992" are disposed on the entire surface of the basket), and materials (e.g., stainless steel, polymers, etc.) of the screens can be changed depending on the desired location and use of the screens, and whether the screens 930, 930', 930" will be cleaned during processing. For example, a screen with larger perforations may be used in tandem with a screen with smaller perforations to remove different materials at different stages of the process and/or different locations along the flow path, as shown in FIGS. 10 and 11.

Figure 10:
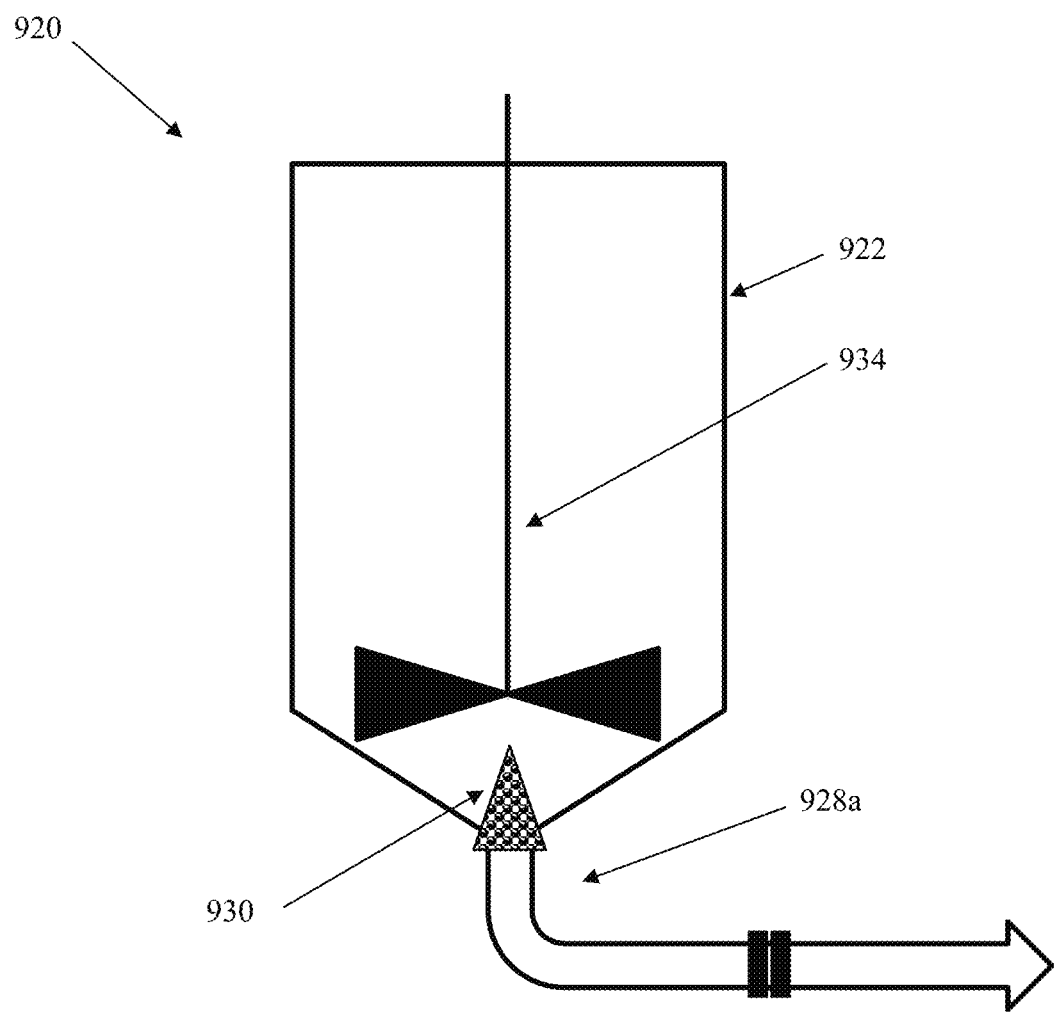
FIG. 10 shows an example of screen placement in a first processing substation in accordance with one or more embodiments of the disclosure.
Figure 11:
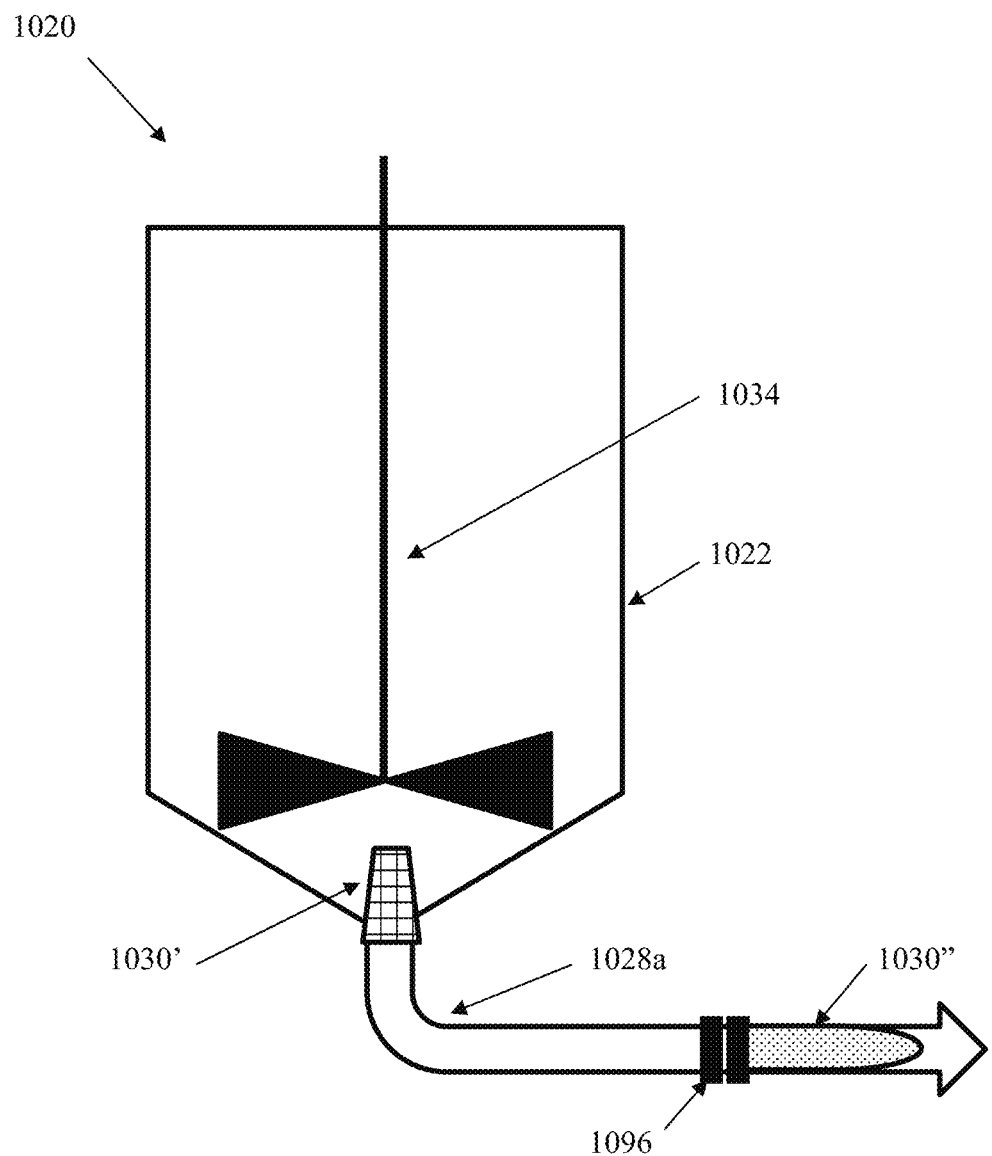
FIG. 11 shows another example of screen placement in a first processing substation in accordance with one or more embodiments of the disclosure.
Figure 12:
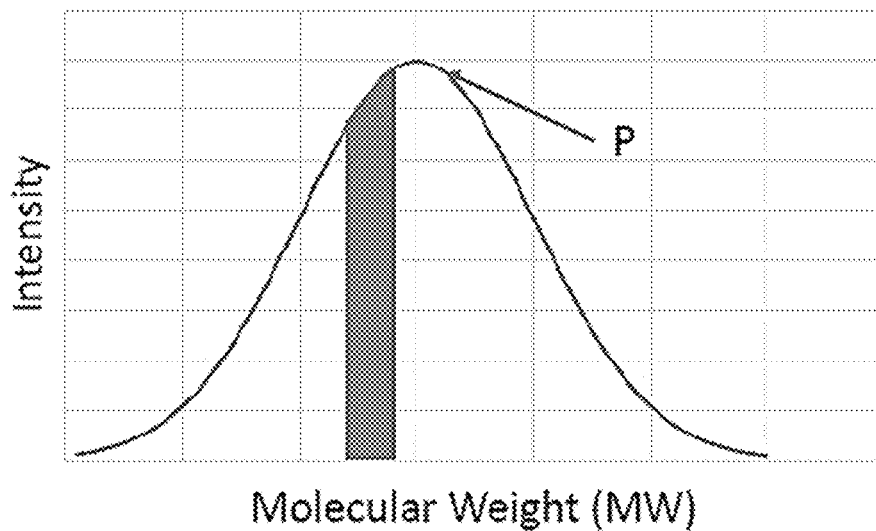
FIG. 12 shows an exemplary graph of the molecular weights (MW) of silk fibroin fragments in an exemplary silk film and/or coating.
Figure 13:
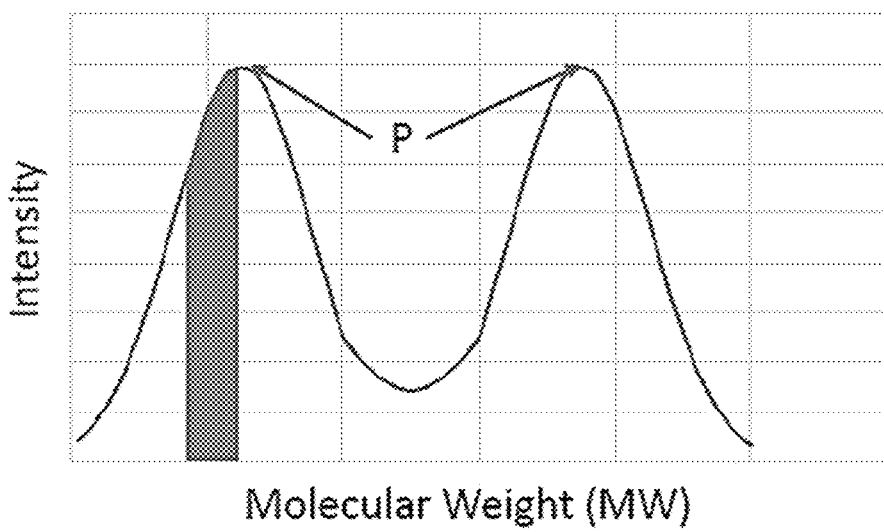
FIG. 13 shows an exemplary graph of the molecular weights (MW) of silk fibroin fragments in an exemplary silk film and/or coating.

FIG. 10 depicts one embodiment of a first processing substation 920 (with or without agitation equipment 934), where a single screen 930 is positioned at the bottom of the reactor vessel 922 just before the outlet 928a. FIG. 11 depicts another embodiment of a first processing substation 1020 (with or without agitation equipment 1034), where two screens 1030', 1030" are utilized. Specifically, a first screen 1030' is positioned at the bottom of the reactor vessel 1022 just before the outlet 1028a, while a second screen 1030" is positioned downstream of the outlet 1028a, for example, secured within the piping exiting the vessel 1020 via a pair of tri-clamps 1096 or similar mechanism that permits for easy removal of the screen 930 for cleaning or replacement. Generally, the screens 930, 930', 930" may be secured via flanges (preferably with gaskets), threaded connections, or other suitable means. Additionally, one or more valves may be incorporated to isolate a screen and and/or provide for easy removal from the system. As previously mentioned, the screens 930', 930" may have different perforation schemes, shapes, etc. to suit a particular application. For example, the screen 1030' disposed within the vessel 1022 may comprise a course mesh that clogs less frequently, requiring fewer cleanings and providing faster draining, while the screen 1030" disposed downstream of the vessel may comprise a finer mesh, but is easily removed for cleaning or replacement. Generally, placement of the screens may be selected to suit a particular application (e.g., ease of insertion and removal, fit within the vessel, mounting configuration, etc.).

What is claimed is:

1. A silk manufacturing system comprising:
   (A) a first processing substation comprising a vessel configured to receive silk inputs, extract silk fibroin proteins therefrom, and produce a silk fibroin-based solution, such that the silk fibroin-based solution is substantially free of sericin, wherein the first processing substation is configured to extract the silk fibroin proteins via degumming, rinsing, and dissolving processes within a single vessel;
   (B) a second processing substation in fluid communication with the first processing substation, the second processing substation configured to receive and purify the silk fibroin-based solution from the first processing substation, wherein the purified silk fibroin-based solution comprises less than about 650 parts per million (ppm) of one or more salts or non-organic particulates;
   (C) wherein the first or second processing substation is further configured to sterilize the silk fibroin-based solution to produce a sterilized silk fibroin-based solution prior to a third processing substation; and
   (D) a third processing substation in fluid communication with the second processing substation, the third processing substation is a spray dryer that is configured to receive and powderize the sterilized silk fibroin-based solution.

2. The system of claim 1, wherein the purified silk fibroin-based solution comprises less than about 400 ppm of the one or more salts or non-organic particulates.

3. The system of claim 1, wherein the powderized silk fibroin-based solution has a water activity level of less than 0.9.

4. The system of claim 1, wherein the silk inputs come from a *Bombyx mori* silkworm.

5. The system of claim 1 further comprising:
   a reservoir disposed between the first and second processing substations and configured to at least one of hold or condition the silk fibroin-based solution; and
   a pump assembly disposed between the first and second processing substations and configured to transfer the silk fibroin-based solution between the first processing substation, the reservoir, and the second processing substation.

6. The system of claim 1, wherein the second processing substation includes at least one spiral wound filtration membrane.

7. The system of claim 1 further comprising a heat exchange system configured to adjust a temperature of the silk fibroin-based solution prior to or after any one of the processing substations.

8. The system of claim 1, wherein the second processing substation is configured to purify the silk fibroin-based solution via diafiltration.

9. The system of claim 1, wherein the second processing substation is configured to purify the silk fibroin-based solution via tangential flow filtration.

10. The system of claim 1, wherein the third processing substation includes a piece of agglomeration equipment.

11. The system of claim 1, further comprising a post-treatment system configured to receive a silk fibroin powder from the third processing substation and to at least one of: condition the silk fibroin powder, test the silk fibroin powder, or package the silk fibroin powder in a food-safe container.

12. A silk manufacturing system comprising:
   (A) a first processing substation comprising a vessel configured to receive silk inputs, extract silk fibroin proteins therefrom, and produce a silk fibroin-based solution, wherein the first processing substation is configured to extract the silk fibroin proteins via degumming, rinsing, and dissolving processes within a single vessel;
   (B) a second processing substation in fluid communication with the first processing substation, the second processing substation configured to receive and purify the silk fibroin-based solution from the first processing substation;
   (C) a third processing substation in fluid communication with the second processing substation, the third processing substation configured to receive and sterilize the purified silk fibroin-based solution; and
   (D) a fourth processing substation in fluid communication with the third processing substation, the fourth processing substation configured to receive and powderize the purified silk fibroin-based solution, wherein the fourth processing substation is a spray dryer.

13. The system of claim 12, wherein the silk inputs come from a *Bombyx mori* silkworm.

14. The system of claim 12, wherein the third processing substation is configured to sterilize the purified silk fibroin-based solution to a food grade standard via microfiltration.

15. The system of claim 12, wherein the third processing substation is configured to sterilize the purified silk fibroin-based solution to a food grade standard via pasteurization.

16. The system of claim 12, wherein the fourth processing substation includes a piece of agglomeration equipment.

17. A silk manufacturing system comprising:
(A) a first processing substation configured to receive silk inputs, extract silk fibroin proteins therefrom, and produce a silk fibroin-based solution, wherein the first processing substation is configured to extract the silk fibroin proteins within a single vessel, the first processing substation comprising:
a reactor vessel comprising a first inlet port configured to receive the raw silk inputs and one or more compounds, a second inlet port configured to receive a solvent, and at least one outlet configured to output the silk fibroin-based solution, wherein the reactor vessel is configured to process the silk inputs by degumming, rinsing, and dissolving the silk fibroin protein from the silk inputs;
a liquid jacket disposed about the reactor vessel and configured to provide heat exchange with the vessel and its contents, wherein the liquid jacket is configured to heat the contents to a temperature of about 50° C. to about 150° C.; and
an agitation mechanism configured to agitate the contents of the reactor vessel;
(B) a second processing substation in fluid communication with the first processing substation, the second processing substation configured to receive and purify the silk fibroin-based solution from the first processing substation, wherein the second processing substation is configured to purify the silk fibroin-based solution via tangential flow filtration, the second processing substation comprising:
a filtration module housing at least one membrane, the module comprising an inlet configured to receive the silk fibroin-based solution including a compound, an outlet configured to output a purified silk fibroin-based solution with a reduced compound amount, and a waste port configured to output a portion of the compound, wherein the filtration module is configured to remove the compound from the silk fibroin-based solution by circulating the silk fibroin-based solution through the filtration module until about 1 diavolume to about at least 12 diavolumes are reached;
(C) a fourth processing substation in fluid communication with the second processing substation, the fourth processing substation configured to receive and sterilize the purified silk fibroin-based solution;
(D) the third processing substation in fluid communication with the fourth processing substation, the third processing substation configured to receive and powderize the sterilized silk fibroin-based solution, wherein the third processing substation is configured to powderize the sterilized silk fibroin-based solution via a spray dryer, and wherein the third process substation includes a piece of agglomeration equipment; and
(E) a post-treatment system configured to receive a silk fibroin powder from the third processing substation and to at least one of: condition the silk fibroin powder, test the silk fibroin powder, or package the silk fibroin powder in a food-safe container.

18. The system of claim 17, wherein the silk inputs come from a *Bombyx mori* silkworm.

19. The system of claim 17, wherein the fourth processing substation comprises a microfiltration module configured to receive the purified silk fibroin-based solution and to remove microbes and reduce turbidity from the purified silk fibroin-based solution.

20. The system of claim 19, wherein the microfiltration module includes two filter stages, the first filter stage having a pore size between about 0.7 µm and about 5 µm and the second filter stage has a pore size between about 0.05 µm and about 0.8 µm, and the purified silk fibroin-based solution passes through the first filter stage prior to passing through the second filter stage.

21. The system of claim 20, wherein the microfiltration module further comprises one or more pumps configured to transfer the purified silk fibroin-based solution between filter stages, between processing substations, to another process as necessary after completing the microfiltration process, or any combination thereof.

22. The system of claim 20, wherein the microfiltration module further comprises one or more holding tanks, wherein the tanks may be configured to provide additional processing, including one or more of storing the purified silk fibroin-based solution, temperature control of the purified silk fibroin-based solution, or adjusting the purified silk fibroin-based solution concentration to address turbidity or sterility levels.

23. The system of claim 17, wherein the reactor vessel is sized to have an aspect ratio of height to diameter as defined by a work volume of about 0.5 to about 5.0.

24. The system of claim 17, wherein the reactor vessel is sized to have an aspect ratio of height to diameter as defined by a work volume of about 0.8 to about 2.0.

25. The system of claim 17, wherein the reactor vessel further comprises a handling structure for controlling at least one of movement or position of the silk inputs within the vessel.

26. The system of claim 17 further comprising a pre-treatment system configured to condition the silk inputs prior to or at introduction to the first processing substation.

27. The system of claim 17, wherein the second processing substation further comprises a heat exchange system to control a temperature of the silk fibroin-based solution or the purified silk fibroin-based solution during processing.

28. The system of claim 17, wherein the filtration module is configured to remove a second compound from the silk fibroin-based solution by circulating the silk fibroin-based solution through the filtration module until about 5 diavolumes to about at least 8 diavolumes are reached.

* * * * *